(12) United States Patent
Jirathitikal et al.

(10) Patent No.: US 7,838,006 B2
(45) Date of Patent: Nov. 23, 2010

(54) VIRAL VACCINE COMPOSITION, PROCESS AND METHODS OF USE

(75) Inventors: Vichai Jirathitikal, Chachoengsao (TH); Aldar Bourinbaiar, College Park, MD (US)

(73) Assignee: Immunitor USA Inc., College Park, MD (US)

( * ) Notice: Subject to any disclaimer, the term of this patent is extended or adjusted under 35 U.S.C. 154(b) by 0 days.

(21) Appl. No.: 12/102,564

(22) Filed: Apr. 14, 2008

(65) Prior Publication Data

US 2009/0226489 A1 Sep. 10, 2009

(51) Int. Cl.
*A61K 39/29* (2006.01)
*C12N 7/04* (2006.01)

(52) U.S. Cl. ............... 424/225.1; 424/184.1; 424/227.1; 424/228.1; 435/236

(58) Field of Classification Search ........................ None
See application file for complete search history.

(56) References Cited

U.S. PATENT DOCUMENTS

| | | | |
|---|---|---|---|
| 3,060,094 A | 10/1962 | Dutcher et al. | |
| 3,859,168 A * | 1/1975 | Barth et al. | 435/236 |
| 4,568,542 A | 2/1986 | Kronenberg | |
| 4,695,454 A | 9/1987 | Prince et al. | |
| 5,506,271 A | 4/1996 | Meruelo et al. | |
| 5,709,995 A * | 1/1998 | Chisari et al. | 435/5 |
| 5,994,083 A | 11/1999 | Felici et al. | |
| 6,024,953 A | 2/2000 | Lathe et al. | |
| 6,245,532 B1 | 6/2001 | Smith et al. | |
| 6,383,806 B1 | 5/2002 | Rios | |
| 6,515,028 B1 * | 2/2003 | Mueller et al. | 514/617 |
| 6,544,528 B1 | 4/2003 | Yamamoto | |
| 6,623,764 B1 | 9/2003 | Sokoll et al. | |
| 6,635,246 B1 | 10/2003 | Barrett et al. | |
| 2002/0001595 A1 | 1/2002 | Sonntag et al. | |
| 2003/0143221 A1 | 7/2003 | Loibner et al. | |

FOREIGN PATENT DOCUMENTS

| | | |
|---|---|---|
| EP | 0775494 | 5/1997 |
| JP | 57175127 | 10/1982 |
| WO | WO-9714434 | 4/1997 |
| WO | WO-0024420 | 5/2000 |
| WO | WO-0047222 | 8/2000 |

OTHER PUBLICATIONS

Berzofsky et al., "Progress on new vaccine strategies against chronic viral infections.," Journal of Clinical Investigation, vol. 114 No. 4, pp. 450-462 (Aug. 2004).*
Huang et al., "Recent development of therapeutics for chronic HCV infection," Antiviral Research, vol. 71 Nos. 2-3, pp. 351-362 (Sep. 2006).*
Hughes et al."Isolation and immunizations with hepatitis A viral structural proteins: induction of antiprotein, antiviral, and neutralizing responses," Journal of Virology, vol. 55 No. 2, pp. 395-401 (Aug. 1985).*
Koziel et al., "Hepatitis C virus (HCV)-specific cytotoxic T lymphocytes recognize epitopes in the core and envelope proteins of HCV," Journal of Virology, vol. 67 No. 12, pp. 7522-7532 (Dec. 1993).*
Prince et al., "Strategies for evaluation of enveloped virus inactivation in red cell concentrates using hypericin," Photochemistry and photobiology, vol. 71 No. 2, pp. 188-195 (Feb. 2000).*
Rascanelli et al., "Presentation of HCV antigens to naive CD8+T cells: why the where, when, what and how are important for virus control and infection outcome," Clincal Immunology, vol. 124 No. 1, pp. 5-12 (E-pub May 2007).*
Rollier et al., "Control of Heterologous Hepatitis C Virus Infection in Chimpanzees Is Associated with the Quality of Vaccine-Induced Peripheral T-Helper Immune Response ," Journal of Virology, vol. 78 No. 1, pp. 187-196 (Jan. 2004).*
Shirai et al., "An epitope in hepatitis C virus core region recognized by cytotoxic T cells in mice and humans," Journal of Virology, vol. 68 No. 5, pp. 3334-3342 (May 1994).*
Tan et al., "Strategies for hepatitis C therapeutic intervention: now and next," Current opinion in pharmacology, vol. 4 No. 5, pp. 465-470 (Oct. 2004).*
C. Henderson (publisher), "Hypericin Profile to Potentially Include Hepatitis C and HIV," AIDS Weekly, Apr. 24, 1995, pp. 7-8.*
Batdelger et al., "Open Label Trial of Therapeutic Hepatitis B Vaccine V-5 Immunitor (V5)Delivered by Oral Route ," Letters in Drug Design & Discovery, vol. 4 No. 8, pp. 540-544 (Dec. 2007).*
Batdelger et al., "Open-label trial of therapeutic immunization with oral V-5 Immunitor (V5) vaccine in patients with chronic hepatitis C," Vaccine, vol. 26 No. 22, pp. 2733-2737 (May 2008).*
Pontisso et al., "Coinfection by hepatitis B virus and hepatitis C virus," Antiviral therapy, vol. 3 Supplement 3, pp. 137-142 (1998—Abstract only).*
Lelie et al., Journal of Medical Virology, vol. 23, pp. 297-301 (1987).
Eisenthal et al., Viral Immunology, vol. 11, pp. 137-145 (1998).
Wladman et al., American Journal of the Medical Sciences, vol. 292, pp. 367-371 (1986).
Avtushenko et al., Journal of Biotechnology, vol. 44, p. 21-28 (1996).
Moldoveanu et al, Journal of Infectious Diseases, vol. 167, pp. 84-90 (1993).
Definition of "immunogen", The On-Line Medical Dictionary, cancerweb.ncl.ac.uk/omd/, 2003.
Jirathitikal et al, HIV Cin Trials 2002;3(1): 21-26.
Jirathitikal et al., Electronic Journal of Biotechnology ISSN: 0717-3458, vol. 6, No. 1, Apr. 15, 2003.

(Continued)

*Primary Examiner*—Zachariah Lucas
(74) *Attorney, Agent, or Firm*—Dykema Gossett PLLC

(57) ABSTRACT

A composition for treating or preventing virus-induced infections is described, along with a process of producing the composition and methods of the composition's use. The composition comprises viral pathogen-infected cell or tissue, or malignantly or immunologically aberrant cells or tissues which has been reduced and/or denatured. The preferred composition is administered across a mucosal surface of an animal suffering or about suffer from infection. The composition is administered as preventive or therapeutic vaccine.

10 Claims, No Drawings

OTHER PUBLICATIONS

Jirathitikal et al., Vaccine 21 (2003) 624-628; Current Pharmaceutical Design, 2003, 9 (18): 1419-1431.
Bourinbaiar et al., Acta virologica 48: 73-78, 2004.
Jirathitikal et al., European Journal of Clinical Nutrition (2004) 58,110-115.
Jirathitikal et al., Journal of Clinical Virology 744 (2004), 1-8.
Bourinbaiar et al., Viral Immunology 16(4), 2003, 427-445.
Epand et al., Biochem. J. (2002) 365, 841-848.
Definition "pill", Dorland's Illustrated Medical Dictionary, mercksource.com/pp/us/cns_health_library_frame.jsp?pg=/pp/us/cns/cns_hl_dorlands.jsp?pg=/pp/us/common/dorlands/dorl and/dmd_a-b_00.htm&cd=3d, (indexed Aug. 2002).
Katakam et al., J Pharm Sci Jun. 1995; 84(6):713-6 (Abstract only).
Meruelo et al., "Therapeutic Agents wtih Dramatic Antiretroviral Activity and Little Toxicity at Effective Doses: Aromatic Polycyclic Diones Hypercin and Pseudohypericin,"Proceedings of the National Academy of Sciences, USA, vol. 85 No. 14, pp. 5230-5234 (Jul. 1988).
Miller, Alan L, "St. John's Wort (*Hypericum perforatum*): clinical effects on depression and other conditions,"Alternative Medicine Review, vol. 3 No. 1, pp. 18-26 (Feb. 1998).
Hepatitis C Vaccine Delivered By Inovio Biomedical's Electroporation System Shows Increased T-Cell Responses And Reduced Viral Loads, Study, Medical News Today, Jul. 4, 2008, Article URL: http://www.medicalnewstoday.com/articles/113964.php.
DNA-based Therapeutic Vaccine for Hepatitis C Posts Encouraging Results, Hepatitis Central, Apr. 29, 2009, URL for Article Source: http://www/biologynews.net/archives/2009/04/23/first_evidence_for_dnabased_vaccination_against_chronic_hepatitis_c.html.

* cited by examiner

VIRAL VACCINE COMPOSITION, PROCESS AND METHODS OF USE

CROSS-REFERENCE TO RELATED APPLICATIONS

The present invention claims priority date from application Ser. No. 09/935,344 filed on Aug. 23, 2001, now abandoned, which claims priority date from provisional U.S. application 60/227,520 filed on Aug. 24, 2000 the disclosure of which are incorporated herein by reference in their entireties.

FIELD OF THE INVENTION

The present invention relates to the therapy and prophylaxis of pathogen-induced infections. In particular the invention relates to antiviral vaccines for oral administration.

BACKGROUND OF THE INVENTION

Infectious diseases are caused by a pathogenic microorganism, like a virus, bacterium, fungus, or the like which enters and propagates in a living body. Common strategies to treat infectious diseases include the administration of an anti-microbial drug (antiviral or antibiotic) to patients suffering from such infections.

In many of cases the pathogenic microorganisms are eradicated or subsided by the action of a chemotherapeutic agent. However, in cases involving infections induced by human immunodeficiency virus (HIV) or herpes virus, the causative agents are not easily eradicated, if at all. Microorganisms may also acquire resistance to drugs. Furthermore, chemotherapeutic agents are generally toxic to varying degrees to patients. For example, an anti-HIV drug, AZT, causes life-threatening toxicity and anemia in about 70% of treated patients. Prolonged treatment results almost invariably in emergence of drug-resistant HIV. As a result, known antibiotics and antivirals have not been entirely satisfactory in terms of their antimicrobial spectrum, antimicrobial activity, behavior in the body, safety, or ability to induce the appearance of drug-resistant microorganisms.

Alternatives to chemotherapy include immunotherapeutic treatment, such as a vaccination. Administration of vaccines to non-infected hosts is referred to as "preventive vaccinating" while administration to already infected hosts has been referred to as "therapeutic vaccination." The term "prevention" includes an attempt to halt the occurrence of a disease or disorder before it happens. The term "therapy" includes an attempt to alleviate the disease or clinical condition of an afflicted subject. The term "immunotherapeutic" includes an attempt to activate or modulate the immune system of the host. The term "subject" or "host" as used hereinafter generally means humans. However, other animal species are equally regarded as suitable hosts or subjects such as for example primates, horses, cows, pigs, sheep, goats, dogs, cats, rodents, fowl, fish, shellfish, crustaceans, worms, etc.

Vaccines usually come in injectable forms and are thus problematic for a widespread use, requiring specialized skills for delivery. As of today very few oral vaccines are known. An example of an oral vaccine is Sabin's attenuated polio vaccine which contains live but less virulent virus. The effect of such oral vaccines is less predictable due to the destructive nature of the digestive milieu and potential danger of virus being reverted to virulent form. It is recognized that on passage to the stomach, the vaccine antigenic component(s) are rapidly inactivated by the gastric pH and digestive enzymes, and thus systemic assimilation through the gut wall is poor or non-existent.

Thus, there remains a long-felt need for better therapies or a vaccine, which preserves its activity despite hostile environment in the stomach and intestines. Such therapies are additionally needs to be free of undesirable properties, such as patient toxicity or even death, the inducement of drug resistance, and the requirement of complicated routes or means of delivery.

The body of a living organism is composed of unit(s) generally known as a "cell." Cells assemble in the body to form what is known as a "tissue." Blood is considered a specialized form of connective tissue being a part of the hematopoietic system. Processed blood products, such as dried deer blood, have been described as an alleged health-invigorating food supplement. See, for example, U.S. Pat. No. 5,637,345 incorporated by reference herein. Whatever its eventual use it is imperative that products be obtained from blood of healthy donors and not from sick or infected donors. Wary of causing or spreading infection, pathogen-contaminated blood or tissue is generally discarded as unsuitable for any use.

Modern vaccines are mostly "acellular" or "subunit" vaccines in which the immunogen is composed of a single bacterial/viral protein or fragment thereof. In some vaccines the immunogen is a nucleic acid of the pathogen or modified or unmodified pathogen itself.

The overwhelming majority of vaccines are administered by injection because it is generally believed that oral administration of a vaccine leads to its destruction in the digestive tract. Nevertheless, the search of the U.S. PTO database for patents containing in their claims keywords such as "vaccine" and "virus" and "oral" results in about 40 patents. The review of such patents reveals that almost every one of them teaches chemically or physically modified forms of the antigen or immunogen, mainly aimed to prevent their degradation in the stomach and gut. Commonly these modifications include entrapment in indigestible polymeric carriers, e.g., U.S. Pat. No. 6,096,291; co-administration of acid neutralizing buffers, e.g., U.S. Pat. No. 5,932,223; co-administration of oil emulsions U.S. Pat. No. 5,885,590; co-administration of absorption enhancing compounds, e.g., U.S. Pat. No. 5,653, 987; orally-administered package that will only dissolve in the host animal's gut, e.g., U.S. Pat. No. 5,676,950; and other complicated and time-consuming safeguarding efforts. Other approaches include expression of foreign, animal antigen (usually a single protein) in genetically modified transgenic plants and oral administration of the recombinant antigen in form of an edible plant, e.g., U.S. Pat. No. 5,889,189. However, in these plants such antigens are not naturally occurring since by definition the animal pathogen cannot infect vegetable tissues. Similarly, U.S. Pat. No. 5,643,577 discloses an oral vaccine comprising an influenza antigen associated with red blood cells. Here again this virus is not natural to the host cell since influenza virus is not capable of infecting red blood cells. Thus, none of the known strategies teaches, discloses, or suggests a composition comprising a pathogen or a plurality of antigens of a pathogen and pathogen-infected tissue, e.g., infected blood, of an animal.

The present inventor describes a simple vaccine comprising a pathogenic antigen and pathogen-infected host tissue. The composition of the invention overcomes the difficulties inherent in prior delivery systems and serves to introduce health modifying agents into and across the mucosal membrane of a human or animal subject. The composition of the invention is administered through a mucosal surface, e.g., enterally by an oral route, to provide significant clinical benefit to infected subjects. In a preferred embodiment, the vaccine is not subjected to any special modification aimed at enhancing the antigen "survival" in a hostile digestive milieu.

The innovative vaccine provides protection both by whole body immunity as well as in the critically important mucosal tissues, such as the cervix, uterus, and rectum where a pathogen often first enters the body during sexual contact or other transmucosal means into person to be infected. Because the gastrointestinal mucosa is a vast interface between the body and the environment, it is the main entry site for many antigens. In tests on animals and patients, the vaccines induces strong reactions by mucosal immune cells in the time frame required to stop infection. At the same time, the vaccines also stimulate strong humoral and cell-mediated reactions to fight pathogen in the blood stream. Thus, as oral vaccines, they work right away on the mucosal cells, then stimulate or downmodulate systemic immunity by raising antibody responses and priming killer cells.

The present invention provides a surprisingly effective and broadly applicable strategy for treating and preventing a variety of microbial infections in diverse host organisms ranging from humans to insects. The same composition is remarkably effective in treating cancer and immune disorders of autoimmune and inflammatory nature.

SUMMARY OF THE INVENTION

The subject of the invention is a pharmaceutical composition which possess immunomodulatory and antiviral activity, as well as the ability to reverse chemotherapeutic drug resistance.

More specifically, the invention contemplates a composition suitable for treating an animal infected with a pathogen or preventing a pathogen-induced infection, the composition comprising a first component comprising denatured antigen of an infection-inducing pathogen and a second component comprising denatured tissue derived from a pathogen-infected animal.

The simplest operating form of the invention is the composition comprises a denatured tissue derived from a pathogen-infected animal and which contains pathogen and components thereof. The donor pathogen-infected animal may be of the same or different species as the animal to be treated or vaccinated. Preferably, the antigen used in the composition comprises a cell, a nucleic acid, a pathogen, an amino acid, an oligopeptide, a peptide, a protein, a glycoprotein, a lipid, a lectin, an oligosaccharide, a lipoprotein, or is an antigen derived therefrom. While any tissue is useful for preparing the composition, a preferred tissue is comprised of blood or components thereof. Blood can be obtained from pathogen-infected subjects. It also can be obtained from rejected blood batches that have been found contaminated with a pathogen, e.g., HIV, (from Blood Banks or organizations like the Red Cross) or from umbilical cord blood from HIV-positive delivering mothers.

In one aspect the present invention provides a non-infectious immunotherapeutic containing viral particles devoid of outer envelope proteins or containing selected antigens isolated from a virus. There is also provided a vaccine effective against HIV. In other aspect, the immunogen is useful for immunizing an individual in need thereof and who is infected by a virus including HIV, so as to induce immunoprotective factors protective against progression of the infection. In another aspect, the vaccine is useful for vaccinating an individual not previously infected with HIV in order to prevent subsequently acquired infection. In another aspect, there is provided a method of rendering a viral immunogen non-infectious. The immunogen may also be used to produce antibodies for passive immunotherapy, alone or in conjunction with active immunotherapy, in individuals infected with a retrovirus, including HIV.

The invention also contemplates a composition for treating or preventing a disease, especially a malignant disease in a host afflicted or about to be afflicted with the same. In this situation instead of pathogen the preferred antigen is derived from malignant cells or tissues. Thus, present invention relates to prophylactic and therapeutic methods of anti-tumor immunization. For example these methods can cross-prime a mammalian host to natural MHC class I or II restricted tumor antigens with tumor antigen. A primary tumor is resected from the patient and a population of tumor cells are cultured in vitro. These cultured tumor cells are optionally loaded with an artificial target antigen. The tumor cells are then inactivated and introduced into the patient. This priming can be simultaneous or subsequent to a direct immunization of the patient with the same or substantially the same artificial target antigen. This method of coupled host immunization promotes a tumor specific cell-mediated immune response against multiple, undefined natural tumor antigens expressed on the unmodified tumor cell surface.

While the preferred vaccine is a multivalent, oral vaccine more specifically-targeted vaccines consisting of one or few select tumor antigens are also contemplated. Such tumor associated antigens can comprise oncofetal antigens, melanoma MPG, melanoma p97, carcinoma Neu oncogene product, members of the MAGE family, the BAGE family, the DAGE/Prame family, the GAGE family, the RAGE family, the SMAGE family, NAG, Tyrosinase, N-acetylglucosaminyltransferase-V, CQA 72/4, Laminin-P1, Yale Col. Sr. Factor, Urinary gonadotropin Peptide (UGP), hCG and chains thereof, Melan-A/MART-1, PSA, carcinoembryonic antigen (CEA), gp100, MUC-1, MUC-2, TRP-1, beta-catenin, MUM-1, CDK-4, TAG-72, CA-125, AMFr, M-344, 19a21 1, erb-2, p15, p21 of ras, mutated p53, Bcr/Abl breakpoint peptide, HER-2/neu, PD-41, TCSF, GA733-2, HPV16 E7 or E6, MZ2-E, B7.1, B7.2, HOM-MEL-40, HOM-MEL-55, NY-COL-2, HOM-HD-397, HOM-RCC-1.14, HOM-HD-21, HOM-NSCLC-11, HOM-MEL-2.4, and HOM-TES-11 or one or more genes or DNA sequences encoding same.

As an anti-tumor agent, the instant composition is useful in treating solid tumors and malignancies of lymphoreticular origin. For example, the composition's utility for treatment of solid tumors includes: cancers of the head and neck, including squamous cell carcinoma; lung cancer, including small cell and non-small cell lung carcinoma; mediastinal tumors; esophageal cancer, including squamous cell carcinoma and adenocarcinoma; pancreatic cancer; cancer of the hepatobiliary system, including hepatocellular carcinoma, cholangiocarcinoma, gall bladder carcinoma and biliary tract carcinoma; small intestinal carcinoma, including adenocarcinoma, sarcoma, lymphoma and carcinoids; colorectal cancer, including collon carcinoma and rectal carcinoma; metastatic carcinoma; cancers of the genitourinary system, including ovarian cancer, uterine sarcoma, and renal cell, ureteral, bladder, prostate, urethral, penile, testicular, vulvar, vaginal, cervical, endometrial, and fallopian tube carcinoma; breast cancer; endocrine system cancer; soft tissue sarcomas; malignant mesotheliomas; skin cancer, including squamous cell carcinoma, basal cell carcinoma and melanoma; cancer of the central nervous system; malignant bone tumors; and plasma cell neoplasms.

The route of administration may be any route. A preferred mode of administration comprises an enteral route, including mucosal administration of the composition. The method comprises contacting a mucosal surface of the animal in need of such composition with an effective amount of a denatured antigen derived from the tissues of an animal infected with said pathogen. Suitable mucosal surfaces include, but are not limited to, nasal, buccal, oral, vaginal, cervical, ocular, auditory, pulmonary tract, urethral, digestive tract, skin, mucocutaneous, anal, cloacal, rectal surface, and the like.

The present invention includes any pathogen. Examples include, but are not limited to, a virus, a viroid, a bacterium, a *rickettsia*, an acoxiella, a prion, a mycoplasma, or a fungus. Moreover, the virus can be influenza virus, cytomegalovirus, avian leukosis-sarcoma virus (ALV), Rous Sarcoma virus (RSV), Mammalian C-type Murine leukemia virus (MLV), Feline leukemia virus (FeLV), simian sarcoma virus (SIS), B-type viruses like Mouse mammary tumor virus (MMTV), D-type viruses like Mason-Pfizer monkey virus (MPMV), Simian AIDS viruses (SRVs), HTLV-BLV group such as Human T-cell leukemia virus (HTLV), Simian T-cell leukemia virus (STLV), bovine leukemia virus (BLV). Lentivirinae comprise Human immunodeficiency virus (HIV-1 and HIV-2), Simian immunodeficiency virus (SIV), Feline immunodeficiency virus (FIV), Visna/maedi virus (MV), Equine infectious anemia virus (EIAV), Caprine arthritis-encephalitis virus (CAEV). Spumavirinae or "Foamy viruses" like Human (HSRV), Simian (SSRV), Feline (FSRV), Bovine (BSRV), Murine (MSRV), endogenous retroviruses (ERV), papilloma virus, respiratory syncytial virus, poliomyelitis virus, pox virus, measles virus, arbor virus, Coxsackie virus, herpes virus, hantavirus, hepatitis virus, Baculovirus, mumps virus, circovirus, vichaivirus, arenavirus, or rotavirus. A bacteria may be a member of the genus *Neisseria, Aerobacter, Pseudomonas, Porphyromonas, Salmonella, Escherichia, Pasteurella, Shigella, Bacillus, Helibacter, Corynebacterium, Clostridium, Mycobacterium, Yersinia, Staphylococcus; Bordetelia, Brucelia, Vibrio, Streptococcus, Plasmodium, Schisostoma, Candida*. Any microbial infections, which are present and/or transmitted as Zoonoses, Cyclozoonoses, Metazoonoses, Saprozoonoses, Anthropozoonoses, Zooanthropozoonoses and Amphixenoses, are encompassed by the present invention. The invention in addition to whole pathogens also encompasses a single antigen or a plurality of antigens from such pathogens, e.g., HIV antigens: gp160, gag, pol, Nef, Tat, and Rev; the malaria antigens: CS protein and Sporozoite surface protein 2; the Hepatitis B surface antigens: Pre-S1, Pre-S2, HBc Ag, and HBe Ag; the influenza antigens: HA, NP and NA; Hepatitis A surface antigens; the Herpes virus antigens: EBV gp340, EBV gp85, HSV gB, HSV gD, HSV gH, HSV early protein product, cytomegalovirus gB, cytomegalovirus gH, and IE protein gp72; the respiratory syncytial virus antigens: F protein, G protein, and N protein or fragments thereof.

It is also an object of the present invention to provide various processes of making the composition. A preferred process of producing a pharmaceutical composition useful against pathogen infection comprises reducing step, i.e., drying pathogen-infected tissue and denaturing the resulting dried tissue substantially in the form as it is. The denatured composition can be processed further, if desired. The denaturation step can be conducted by exposing the composition to heat, detergent, acid, or base. Other exemplary steps in making for example an anti-virus composition include but are not limited to culturing cells from a cell line on a cell culture medium, inoculating the cells with the virus in the presence of a viral multiplication medium, propagating and multiplying the virus, harvesting cells and the viral multiplication medium, optionally subjecting the composition to the purification preparation like washing, ion-exchange chromatography, adsorption chromatography and/or gel permeation, denaturing the composition by physical and/or chemical means, and formulating and incorporating the obtained composition in a pharmaceutical form.

In accordance with the object of the invention a process is contemplated which comprises rapid freezing and/or drying of aqueous products, pharmaceutical products, biologicals, blood products, tissues and the like. The drying step may include freeze-drying, spray-drying, flash-drying, heat-drying, or vacuum-drying.

It is a further object of the invention to provide uniform freezing and freeze-drying of all containers or vials in a batch to minimize product variation from vial to vial.

Where the composition is provided as a powder, its dosage may varied according to the route of administration, the age, body weight and condition of the patient, and the type of the disease. Generally, the preferred daily dose of the composition itself ranges from about 0.00001 to 150 g per subject. Most preferably, a daily dose of 0.02 to 5 g is given in 1 to 3 divided doses. Instead of daily doses the composition can be given in less frequent regimen, e.g., once every 3 days, once weekly, once monthly, once every 3 months, or once every 6 months as needed. Doses given once a year or less frequently as required by exigencies of the therapy or patient's condition are also contemplated as equally suitable.

For the above indications the dosage may also vary depending on the mode of administration or on the type of therapy desired. Generally, however, dosage levels between 0.0001 and 100 mg/kg body weight daily are administered to patients to obtain effective clinical benefit. Usually, dosage forms suitable for oral, nasal, pulmonar or transdermal administration comprise from about 0.0001 mg to about 100 mg, preferably from about 0.001 mg to about 50 mg of the composition admixed when necessary with a pharmaceutically acceptable carrier or diluent. When administered transdermally the composition can be delivered under conditions of both constant current (iontophoresis) and constant voltage (electroporation).

Optionally, the pharmaceutical composition of the invention may further comprise one or more compounds exhibiting a different mechanism of activity, e.g., an antibiotic or antiviral or any other pharmacologically active material as deemed necessary by the practitioner.

For example, the composition can be used in combination with any of current or future AIDS drugs. Examples of such drugs include those belonging to reverse transcriptase, integrase, protease, fusion, adhesion, chemokine and other inhibitors like herbal drugs, interleukins like interferon or IL-2 and including but not limited to ZIAGEN Abacavir; PREVEON Adefovir; AGENERASE Amprenavir; RETROVIR Zidovudine; VIDEX Didanosine; HIVID Zalcitabine; ZERIT Stavudine; SUSTIVA Efavirenz; EPIVIR Lamivudine; INVIRASE Saquinavir; FORTOVASE CRIXIVAN Indinavir; NORVIR Ritonavir; RESCRIPTOR Delavirdine; VIRACEPT Nelfinavir; and VIRAMUNE Nevirapine as representative AIDS drugs.

The compositions of the invention can be administered to humans and valuable animals or plants to prevent infection and generally for restoring health.

These and other objects, advantages and purposes of the invention will be appreciated from the following description and accompanying drawings illustrating preferred embodiments of the invention.

BRIEF DESCRIPTION OF THE DRAWINGS

No drawing is provided.

DETAILED DESCRIPTION OF THE INVENTION

Various microorganisms cause devastating diseases to the host. This invention contemplates a simple preventive and/or therapeutic measure against them. Those of particular concern are following: *Bacillus anthracis, Bordetella pertussis, Borrelia* spp., *Brucella* spp., *Campylobacter* spp., *Clostridium botulinum, Clostridium difficile, Clostridium tetani, Corynebacterium diphtheriae, Erysipelothrix rhusiopathiae, Escherichia coli, Francisella tularensis, Haemophilus ducreyi, Helicobacter pylori, Leptospira* spp., *Mycobacterium tuberculosis. M. bovis, Mycobacterium leprae, Mycoplasma* spp., *Neisseria gonorrhoea, Neisseria meningitidis, Pasteurella* spp., *Pseudomonas mallei* (*Burkholderia mallei*), *Pseudomonas pseudomallei* (*Burkholderia pseudomallei*), *Rochalimaea, Salmonella typhi, Salmonella* spp. other than *S. typhi, Serratia marcescens, Shigella* spp., *Streptobacillus moniliformis, Streptococcus* spp., *Treponema pallidum, Vibrio cholerae, Yersinia pestis; Chlamydias, Coxiellas* and *Rickettsias: Chlamydia psittaci, Chlamydia trachomatis, Coxiella bumetii, Rickettsia mooseri, Rickettsia orientalis, Rickettsia prowazeki, Rickettsia rickettsii*; Viruses: Adenovirus, Korean haemorrhagic fever virus, Hantavirus, Argentine haemorrhagic fever virus, Junin virus, Aujeszky disease virus, Pseudorabies virus, Herpesvirus, Chikungunya virus, Cowpox virus, Coxsackieviruses, Creutzfelt-Jacob Disease agent (prion), Crimea Congo haemorrhagic fever virus, Cytomegalovirus, Dengue virus, Eastern encephalitis virus, Ebolavirus, Ganjam virus, Hantavirus, Hepatitis A virus, Hepatitis B virus, Hepatitis C virus, Hepatitis G, Herpesvirus simiae (B virus), Human immunodeficiency virus, Junin virus, Kyansanur Forest disease virus, Lassa fever virus, Louping ill virus, Lymphocytic choriomeningitis virus, Marburg virus, Milkers nodule virus, Newcastle disease virus, Omsk haemorrhagic fever virus, Orf virus, Parvovirus, Poliovirus, Pseudorabies, Rabies virus, Rift Valley fever virus, Russian Spring-Summer encephalitis virus, Sabia virus, St Louis encephalitis virus, Vaccinia virus, Venezuelan equine encephalitis, Vesicular stomatitis virus, Western equine encephalitis virus, Yelllow fever virus; Fungi: *Aspergilllus* spp., *Blastomyces dermatitidis, Coccidioides immitis, Cryptococcus neoformans, Microsporum* and *Trichophyton* spp., *Histoplasma capsulatum, Sporothrix schenkii*; Endoparasites like *Ancylostama, Strongylus, Trichostrongylus, Haemonchus, Ostertagia, Ascaris, Toxascaris, Uncinaria, Trichuris, Dirofilaria, Toxocara, Necator, Enterobius, Strongyloides* and *Wuchereria; Acanthamoeba* and other amoebae, *Cryptosporidium, Fasciola, Hartmanella, Acanthamoeba, Giardia lamblia, Isospora belli, Leishmania, Naegleria, Plasmodium* spp., *Pneumocystis carinii, Schistosoma* spp., *Toxoplasma gondii*, and *Trypanosoma* spp., among many others.

To solve this important health issue, the present invention provides a composition containing pathogenic antigen denatured thermally and/or under acidic or alkaline conditions or other chemical means and derived from infected tissues or cells of animals of the same species as the animal intended to be treated. In another embodiment the species of animals as the source of tissue or cell are different.

One can readily contemplate a variety of infections and clinical conditions that can be dealt with using the teachings of the present invention. These infections include, but are not limited to, Mediterranean fever, undulant fever, Malta fever, contagious abortion, epizootic abortion, Bang's disease, Salmonella food poisoning, enteric paratyphosis, Bacillary dysentery, Pseudotuberculosis, plague, pestilential fever, Tuberculosis, Vibrios, Circling disease, Weil's disease, Hemorrhagic jaundice (*Leptospira icterohaemorrhagiae*), canicola fever (*L. canicola*), dairy worker fever (*L. hardjo*), Relapsing fever, tick-borne relapsing fever, spirochetal fever, vagabond fever, famine fever, Lyme arthritis, Bannworth's syndrome, tick-borne meningopolyneuritis, erythema chronicum migrans, Vibriosis, Colibacteriosis, colitoxemia, white scours, gut edema of swine, enteric paratyphosis, Staphylococcal alimentary toxicosis, staphylococcal gastroenteritis, Canine Corona Virus (CCV) or canine parvovirus enteritis, feline infectious peritonitis virus, transmissible gastroenteritis (TGE) virus, Hagerman Redmouth Disease (ERMD), Infectious Hematopoietic necrosis (IHN), porcine *Actinobacillus* (Haemophilus) pleuropneumonia, Hansen's disease, Streptotrichosis, Mycotic Dermatitis of Sheep, Pseudoglanders, Whitmore's disease, Francis' disease, deerfly fever, rabbit fever, O'Hara disease, Streptobacillary fever, Haverhill fever, epidemic arthritic erythema, sodoku, Shipping or transport fever, hemorrhagic septicemia, Ornithosis, Parrot Fever, Chlamydiosis, North American blastomycosis, Chicago disease, Gilchrist's disease, Cat Scratch Fever, Benign Lymphoreticulosis, Benign nonbacterial Lymphadenitis, Bacillary Angiomatosis, Bacillary Peliosis Hepatis, Query fever, Balkan influenza, Balkan grippe, abattoir fever, Tick-borne fever, pneumorickettsiosis, American Tick Typhus, Tick-borne Typhus Fever, Vesicular Rickettsiosis, Kew Gardens Spotted Fever, Flea-borne Typhus Fever, Endemic Typhus Fever, Urban Typhus, Ringworm, Dermatophytosis, Tinea, Trichophytosis, Microsporosis, Jock Itch, Athlete's Foot, *Sporothrix schenckii*, dimorphic fungus, Cryptococcosis and histoplasmosis, Benign Epidermal Monkeypox, BEMP, Herpesvirus simiae, Simian B Disease, Type C lethargic encephalitis, Yellow fever, Black Vomit, hantavirus pulmonary syndrome, Korean Hemorrhagic Fever, Nephropathia Epidemica, Epidemic Hemorrhagic Fever, Hemorrhagic Nephrosonephritis, lymphocytic choriomeningitis, California encephalitis/La crosse encephalitis, African Hemorrhagic Fever, Green or Vervet Monkey Disease, Hydrophobia, Lyssa, Infectious hepatitis, Epidemic hepatitis, Epidemic jaundice, Rubeola, Morbilli, Swine and Equine Influenza, Fowl Plague, Newcastle disease, Piroplasmosis, toxoplasmosis, African Sleeping Sickness, Gambian Trypanosomiasis, Rhodesian Trypanosomiasis, Chagas's Disease, Chagas-Mazza Disease, South American Trypanosomiasis, *Entamoeba histolytica*, Balantidial dysentery, cryptosporidiosis, giardiasis, Cutaneous leishmaniasis: Chiclero ulcer, espundia, pianbols, uta, and buba (in the Americas); oriental sore, Aleppo boil (in the Old World); Bagdad boil, Delhi boil, Bauru ulcer, Visceral leishmaniasis: kala-azar, Microsporidiosis, Anisakiasis, Trichinosis, Angiostrongylosis, eosinophilic meningitis or meningoencephalitis (*A. cantonensis*), abdominal angiostrongylosis (*A. costaricensis*), Uncinariasis, Necatoriasis, Hookworm Disease, Capillariasis, Brugiasis, Toxocariasis, Oesophagostomiasis, Strongyloidiasis, Trichostrongylosis, Ascaridiasis, Diphyllobothriasis, Sparganosis, Hydatidosis, Hydatid Disease, *Echinococcus granulosis*, Cystic hydatid disease, Tapeworm Infection, *Schistosoma* and the like. Malignant diseases caused by infectious pathogens are contemplated as well. The examples of such diseases include for example Burkitt lymphoma caused by EBV, Rous sarcoma caused by Rous retrovirus, Kaposi' sarcoma caused by herpes virus type 8, adult T-cell leukemia caused by HTLV-I retrovirus, or hairy cell leukemia caused by HTLV-II, and many other tumors and leukemias caused by infectious agents and viruses.

In addition diseases which are not caused by a known pathogen, especially malignant or immunological diseases are contemplated as suitable for treating or preventing by the composition of the invention. Nonlimiting examples of these diseases comprise leukemias like acute leukemia, acute lymphocytic leukemia, acute myelocytic leukemias like myeloblastic, promyelocytic, myelomonocytic, monocytic, erythroleukemia, chronic leukemia like chronic myelocytic or granulocytic leukemia, chronic lymphocytic leukemia, polycythemia vera, Sezary cell leukemia, lymphoma, Hodgkin's disease, non-Hodgkin's disease, multiple myeloma, Waldenstrom's macroglobulinemia, heavy chain disease, solid tumors like sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, Kaposi's sarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, mycosis fingoides, pagetoid reticulosis among many others.

Instant composition is equally suitable as an immunomodulator for treating immune disorders like inflammatory and autoimmune diseases. As used herein, the terms "immunomodulator" and "immunomodulating" encompass the activity of enhancing or restoring the subject's immune system, as evidenced by measurable clinical parameters and/or the patient's improved ability to combat infection or disease, and the ability to heal tissue. Hence, immunomodulation encompasses improvement of the immune system due to an immunodeficient state (for example, caused by removal of the thymus), and/or an immunodepressed state (for example, caused by exposure to radiation). Furthermore, the present invention provides for modulation of the immune system by lowering blood parameters and other indicia of the immune state if these indicia are abnormally elevated or suppressed. The present invention encompasses the therapeutic method of treating the immunodeficient, immunodepressed or wrongly activated immune state per se, thus providing prophylaxis against infection and disease, as well as a treatment of infection, disease or wound indirectly by enhancing the immune system. It is therefore an object of the present invention to provide pharmaceutical compositions which have broad immunomodulating activity, as well as activity for other uses such as treatment of infections, disease and wounds (burns, frost bites, and the like), enhancement of metabolic processes, and many other uses.

Inflammation plays a critical role in elimination of foreign substances. Generally, recognition components of the host's immune system bind to epitopes of the foreign matter, activating an amplification system that includes the complement cascade, cytokines, the coagulation cascade, lipid mediators and amines produced by mast cells. These activated systems and components alter blood flow, increase vascular permeability, augment adherence of circulating leukocytes to vascular endothelium, promote migration of leukocytes into tissues, and stimulate leukocytes to destroy the foreign substance. By providing orally foreign substances incorporated in the present composition an inflammatory reaction is substantially subsided. The suitable inflammatory condition favorably treatable by present composition is an immunoinflammatory condition like transplant rejection, sepsis, ARDS, asthma, trauma, oxidative stress, nitric oxide-related inflammatory reaction, cell death or apoptosis, Alzheimer's disease, Parkinson's disease, neurodegenerative disease, demyelinating disease, HIV dementia, tumor angiogenesis, irradiation damage, drug allergy, ischemia, reperfusion, periodontitis, gingivitis, rhinitis, allergic conjunctivitis, eczema, anaphylaxis, restenosis, stroke, congestive heart failure, endometriosis, atherosclerosis, endosclerosis, corneal ulceration, retinopathy, wound healing, gout, acute phase response, meningitis, migraine, malignant ascites, malignant pleural effusion, scleroderma, cirrhosis, keloids, adhesions and hypertrophic scars, ankylosing spondylitis, Burger's disease, periarteritis nodosum, hemolytic anemia, aplastic anemia, pure red cell anemia, idiopathic thrombocytopenia, urticaria, endometrial hyperplasia, benign prostatic hypertrophy, proliferative vitreal retirropathy, dysplasias, skin infection, pyoderma, furunculitis, cellulitis, acne, infralymphatic infection, lymphangitis, gynecological infection, pelvic inflammatory disease, cervicitis, vaginitis, tubo-ovarian abscess, adnexal abscess, acute respiratory disease, sinusitis, parsinusitus, periapical granuloma, burn, frost bite.

The development of immunologic responsiveness to self is called autoimmunity. The development of autoimmunity usually involves the breakdown or circumvention of self-tolerance and by orally administering to a host the self-antigens will restore said self-tolerance. It has been surprisingly discovered that upon oral administration benign self-antigens involved in autoimmunity as opposed to orally administered malignant or pathogenic antigens will trigger beneficial immune tolerance reaction. Representative autoimmune diseases include allergy, alopecia greata, ulcerative colitis, Mooren's ulcer, psoriasis, systemic lupus erythematosus, rheumatoid arthritis, bursitis, rheumatoid vasculitis, joint rigidity, collagen disorders, periarteritis nodosum, Wegener's granulomatosis, polyarteritis nodosa, chronic graft versus host disease, Waldenstrom's macroglobulinemia, hyperviscosity syndrome, monoclonal gammopathy of undetermined origin, POEMS syndrome, myeloma, fibromyalgia, macroglobulinemia, cold agglutinin disease, myasthenia gravis cryptogenic fibrosing alveolitis, reactive arthritis, Reiter's arthritis, polymyositis, dermatomyositis, localized scleroderma, cutaneous scleroderma, systemic scleroderma, Sjorgen's syndrome, Raynaud's phenomenon, Behcet's disease, Kawasaki's disease, Hashimoto's thyroiditis, Steven-Johnson syndrome, idiopathic burning mouth, aphthous ulceration, idiopathic sprue, hyperimmunoglobin E, sarcoidosis, antiglomerular renal membrane disease, primary iary sclerosis, primary sclerosing cholangitis, ulcerative colitis, Crohn's disease, juvenile onset diabetes, insulin dependent diabetes mellitus, juvenile dermatomyositis, autoimmune or chronic hepatitis, multiple sclerosis, idiopathic inflammatory bowel disease, keratoconjunctivitis sicca, vernal keratoconjunctivarthritis, sympathetic ophthalmia, uveitis, uveoretinites, glomerulonephritis, unities, atopic dermatitis, epidermolysis bullosa, eczematous dermatitises, seborrhoeic dermatitis, lichen planus, pemphigus, bullous pemphigoid, cutaneous eosinophilia, acne, Darier's disease, iethyosis.

The instant composition can be prepared by a variety of different methods, which have commonly been utilized in food industry to prepare blood meals or dried foods in general. The various methods can comprise flash Dried (Ring Dried and Drum Dried), Spray Dried, Freeze Dried, and Conventional Cooker Dried. The term "drying" is a collective term that can describe several different drying processes.

Typically, a large portion of the moisture (water) is mechanically removed. The subsequent semi-solid mass is then transferred to another compartment (flash dryer) where the more tightly bound water is rapidly removed. One skilled in the art would know how to properly adjust dryer to obtain high quality product. These processes are extensively used in the rendering industry. As with any ingredient, proper plant procedures and optimum temperature control will positively influence the quality of the blood meal produced. Properly processed Ring Dried Blood Meal is the preferred method of drying by many nutritionists due to its consistent quality. The Ring Dried process produces a product that is almost black in color and should be of a very fine particle size. Spray Drying is a process commonly used in the drying of whey proteins and dried fats. Spray Dried Blood Meal produces a product that is readily soluble in water. Therefore, it can be used in products by patients who may have difficulty of swallowing solid formulations of the composition. Spray Drying is an acceptable processing method, but is less common and more expensive than Flash Dried Blood Meal. Conventional Cooker Dried Blood Meal is the oldest of the blood processing methods. This type of Blood Meal is processed in a batch type rendering cooker and there may be a great variation in the biological potency of the composition.

An alternative preparation process requires an acid hydrolysis (e.g., HCl hydrolysis or carbon dioxide hydrolysis) to produce a liquid product. The product is then condensed under elevated temperatures and vacuum to remove excess moisture and increase solid concentration. The concentrated liquid is then dried. The resulting product is a flowable dry powder, which has significant levels of high quality soluble protein and fat. Residual lipids in such preparation can be stabilized with an antioxidant such as BHT, TBHQ, or Ethoxyquin to prevent the formation of peroxides. In general, antioxidant addition will ensure adequate storage life. Amongst antioxidants used, BHA and TBHQ, at a concentration of about 30 ppm, are the most effective. Oxidation of treated meats during a 5-week storage period at 4° C. is delayed as monitored by the TBA test. Other additives like butylated hydroxyanisole, BHA; tertbutylhydroquinone, TBHQ; sodium tripolyphosphate, STPP; sodium pyrophosphate, SPP; sodium hexametaphosphate, SHMP; disodium salt of diethylenediaminetetraacetic acid, sodium EDTA; sodium ascorbate, SA; and sodium hypophosphite, SHP; 2-thiobarbituric acid (TBA), Ellagic Acid, Eugenol, Isoeugenol, Quercetin, Kaempferol, Rutin, Cinnamic Acid, Coumaric Acid, Ferulic Acid, Caffeic Acid, Vanillic Acid, Gallic Acid, Syringic Acid, Chlorogenic Acid, and 3,5-dimethoxy-4-hydroxycinnamic acid (DMHC) among others.

By alternative feature of the novel composition of the invention, the composition can be in form of emulsion-type product and made into a food like frankfurters, wieners, or restructured meats or slices or chunks of meat and pieces as well as large cuts, prepared seafoods or other hybrid products and the cooked cured meat or any of the variants. For example a process for producing a food product simulating meat from an anticoagulant-treated, coagulable blood fluid can be carried out by controlled, chemically-stimulated coagulation of the blood fluid under controlled temperature conditions. This can comprise coagulating an anticoagulant-treated, coagulable blood fluid, whole animal blood, a plasma phase of animal blood, a mixture of a hemoglobin phase of animal blood and a plasma phase of animal blood, a mixture of whole animal blood and a plasma phase of animal blood; a mixture of whole animal blood and a hemoglobin phase of animal blood or a mixture of whole animal blood, a plasma phase of animal blood and a hemoglobin phase of animal blood, in the presence of an exudation-inhibiting agent and a coagulation stimulant, both present in effective amounts, while maintaining the blood fluid at a temperature within about 10° C., either above or below the physiological temperature of the animal from which blood has been derived to chemically induce coagulation, and then recovering the resultant coagulate.

Where the vaccine is intended for animal or veterinary use, the vaccine is conveniently administrable with the animal feed, such as grain or food pellets, bait, or in the animal drinking water. The vaccine composition may also be incorporated into a food meal or may be topically applied, i.e., sprayed onto meal.

The medical preparation forms can be solid or fluid. In addition, it is possible to administer the active agent with vehicles, diluents and additives which are usual in biopharmaceutics, are pharmacologically harmless and are compatible with the active ingredient. Additives can include fillers, dispersants, binding agents, moisteners, stabilizers, lubricants, emulsifiers, sweeteners, flavors and similar. These additives can additionally include for example melantine solutions, pectin solutions, lactose, sodium chloride, talcum, starch, boric acid, paraffin oil, paraffin, stearic acid and its derivatives, cocoa butter, rubber, syrups, licorice extracts, yeast extracts, honey, glycerol, silicious earth, kaolin, magnesium oxide, beeswax and plant oils. Stabilizers, for example, can be added prior to lyophilization these include but not limited to hydrolyzed gelatin, sodium chloride, sodium bicarbonate, human serum albumin, cysteine, sodium glutamate, chelator, sugars like sorbitol, mannitol, dulcitol, sucrose, lactose, maltose or trehalose, and buffers like phosphate or citrate. The use of such media and agents for pharmaceutical active substances is well known in the art and is described by way of example in Remington's Pharmaceutical Sciences, 18th Edition, Mack Publishing Company, Pennsylvania, U.S.A. Except insofar as any conventional media or agent is incompatible with the active ingredient, use thereof in the vaccine compositions is contemplated.

When the composition of the present invention can be used directly for purposes of clinical therapy and prophylaxis it can have the form of an oral preparation or a parenteral preparation. The term "parenteral" includes subcutaneous, intravenous, epidural, irrigation, intramuscular, release pumps, or infusion. Without limiting the composition can be also administered intra-articularly, intrasynovially, intrathecally, periostally, intratumorally, peritumorally, intralesionally, perilesionally, sublingually, buccally, transdermally, topically or by inhalation. It also can be administered as a dressing for a wound or lesion. However, oral administration of the composition is especially preferred. For oral use, the composition of the present invention can be used alone or in combination with pharmaceutically acceptable carriers to form pharmaceutical preparations such as capsules, pills, lozenges, tablets, dragees, sachets, tea bags, granules, powders, coated tablets, sugar coated tablets, wafers, sugar cubes, gels, hydrogels such as particles of a hydrophilic-hygroscopic polysaccharide, foams, suppositories, inhalants, juices, shakes, chewing gum, tooth paste, dentifrice, mouthwash, candies, and emulsions.

Suitable pharmaceutical carriers include, for example, fillers such as lactose, sucrose, mannitol, glucose, starch, sorbitol, glycine, calcium phosphate and microcrystalline cellulose; binders such as starch, casein, gelatin, acacia, glucose, sucrose, sorbitol, mannitol, tragacanth, hydroxypropylcellulose, hydroxypropoxymethylcellulose, carboxymethylcellulose, 2-methyl-5-vinylpyridine/methyl methacrylate/ethylacrylate copolymer, polyvinylpyrrolidone and sodium alginate; alginate gel; lubricants such as stearic acid, hardened oil, magnesium stearate, calcium stearate, polyoxyethylene monostearate, talc, silicon oxide and polyethylene glycol; disintegrators such as potato starch, and starch containing a surfactant or the like; facilitators like magnesium sulphate; and humectants such as sodium lauryl sulfate.

Composition of the present invention can also be administered in the form of liposomes. As is known in the art, liposomes or artificial lipid vesicles are generally derived from phospholipids or other lipid substances. Additionally they can contain muramyl peptide, a metabolizable oil, and optionally an additional emulsifying agent. Liposomes are formed by mono- or multi-lamellar hydrated liquid crystals that are dispersed in an aqueous medium. A typical process for making a liposome preparation comprised of liposomes that contain an encapsulated composition of the invention, comprises hydrating a lipid or liposome formulation with a solution of a material to be encapsulated; providing a plurality of portions of a dry lipid or dry liposome formulation; hydrating each of said plurality of portions with a solution comprising said material to be encapsulated; and combining each of said plurality of portions to form a single liposome preparation, thereby forming a liposome preparation comprising liposomes that contain said encapsulated material. Any nontoxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are well known in the art. For example, cochleates containing biologically relevant molecule component, a negatively charged lipid component, and a divalent cation component. The cochleate has an extended shelf life, even in a desiccated state. Advantageously, the cochleate can be ingested.

Other encapsulating microspheres or vesicles are also known. For example one embodiment is an autogenous vaccine composition comprising protein-lipid vesicles, said protein-lipid vesicles comprising a patient-specific antigen from a patient that is infected with human immunodeficiency virus; immunomodulator which is at least one member selected from the croup consisting of an envelope protein of an animal or human virus, a chemical immunomodulator, interferon alpha, interferon gamma, and interleuken 12; and lipid that forms a protein-lipid vesicle; wherein the patient-specific antigen is prepared by extraction from infected cells, tissue or organs with non-ionic detergent in physiologically balanced buffer.

Another type comprises a biodegradable-biocompatible poly(DL-lactide-co-glycolides. The bulk matrix is produced by a solvent evaporation process and antigen is pre-encapsulated into a conformationally stabilizing hydrophilic matrix consisting of an appropriate mono, di- or tri-saccharide or other carbohydrate substance by lyophilization prior to its final encapsulation into the microsphere by a solvent extraction process employing acetonitrile as the polymer solvent, mineral oil as the emulsion's external phase, and heptane as the extractant.

In yet another embodiment the polymer core matrix is formed from at least two highly water soluble biodegradable polymers, selected for example from starch, crosslinked starch, ficoll, polysucrose, polyvinyl alcohol, gelatine, hydroxymethyl cellulose, hydroxyethyl cellulose, hydroxypropyl cellulose, hydroxypropyl-ethyl cellulose, hydroxypropyl-methyl cellulose, sodium carboxymethyl cellulose, cellulose acetate, sodium alginate, polymaleic anhydride esters, polyortho esters, polyethyleneimine, polyethylene glycol, methoxypolyethylene glycol, ethoxypolyethylene glycol, polyethylene oxide, poly(1,3 bis(p-carboxyphenoxy) propane-co-sebacic anhydride, N,N-diethylaminoacetate, block copolymers of polyoxyethylene and polyoxypropylene. The microspheres are additionally coated with a (D,L lactide-glycolide) copolymer.

The blood powder as one embodiment of the invention can be conventionally put into gelatin hard capsules or formulated into tablets having the instant composition at about 0.5 mg or higher; Magnesium stearate 5 mg, optionally Corn starch at 20 mg and Lactose 194.5 mg. The tablet can contain other ingredients like vitamins, antioxidants and alike. Although a preferred saccharide is lactose, other saccharides can be used, such as sucrose, mannitol, glucose, polyaspartic acid, inositol hexaphosphate (phytic acid), sialic acid, N-acetylneuraminic acid-lactose, inositol, fructose, maltose or galactose. In addition, combinations of saccharides can be used, for example, lactose and mannitol, or sucrose and mannitol. Other sugars like phosphorylated sugars are equally suitable. The concentration of the saccharide can range from about 1% to 80% by weight.

In the case of suppositories, either rectal or vaginal, cacao butter, Witepsol, Subanal, polyethylene glycol, polypropylene glycol, glycerogelatin, gelatin capsules and the like can be used as bases. Other additives include well-known safe antiseptics such as methyl p-hydroxybenzoate, paraben forms, boric acid, propyl p-hydroxybenzoate, butyl p-hydroxybenzoate and butyl hydroxyanisol; and safe colorants. The composition can also be administered as enema or clysters or prepared in a such way that it will be orally administered as a pharmaceutical preparation with colon selective delivery.

In preparing an injection (solution, emulsion or suspension), it is generally sterilized and is preferably made isotonic to the blood. In preparing the solution, emulsion or suspension, there can be used all diluents commonly used in the art, such as water, ethyl alcohol, propylene glycol, ethoxylated isostearyl alcohol, polyoxyisostearyl alcohol and polyoxyethylene sorbitan-fatty acid esters. In this case, the injection may contain sodium chloride, glucose or glycerine in an amount sufficient to make the injection isotonic, and may further contain a solubilizing agent, a buffer solution, a soothing agent, etc. all ordinarily used. The injection may furthermore contain, as necessary, a coloring agent, a preservative, a perfume, a flavoring agent, a sweetening agent and other drugs.

A variety of buffers may be used, depending on the pH range desired, preferably between 7.0 and 7.8. Suitable buffers include phosphate buffer and citrate buffer.

The lyophilized or dehydrated composition of the subject invention can be reconstituted to an aqueous solution using a variety of substances, but are preferably reconstituted using water. In certain instances, dilute salt solutions which bring the final formulation to isotonicity can also be used. In other circumstances solutions can be a fruit juice or milk. In addition, it can be advantageous to use aqueous solutions containing components known to enhance the activity of the reconstituted composition. Such components can include cytokines, such as IL-2, polycations, such as protamine sulfate, or other components, which enhance the efficiency of the composition, e.g., vitamins and minerals. Other enhancing compounds can be sodium salicylate, sodium lauryl sulphate, disodium ethylenediaminetetraacetic acid (disodium EDTA), oleic acid, linoleic acid, monoolein, lecithin, lysolecithin, deoxycholate, sodium deoxycholate, chenodeoxycholate, taurodeoxycholate, glycochenodeoxycholate, polyoxyethylene X-lauryl ether wherein X is from 9 to 20, sodium tauro-24, 25-dihydrofusidate, polyoxyethylene ether, polyoxyethylene sorbitan esters, p-t-octylphenoxypolyoxyethylene, N-lauryl-.beta.-D-maltopyranoside, 1-dodecylazacycloheptane-2-azone and phospholipids, wherein the amount of each of the enhancing compounds is present in a concentration of from 1 to 10 w/w % of the total formulation. Preferably each of the enhancing compounds is present in a concentration of from 0.0005 to 3.5 w/w %

Lyophilized or dehydrated composition can be reconstituted with any convenient volume of water or the reconstituting agents noted above that allow substantial, and preferably total solubilization of the lyophilized or dehydrated sample.

If the composition is an aqueous solution it can contain a neutral salt which is used to adjust the final formulation to an appropriate iso-osmotic salt concentration. Suitable neutral salts include sodium chloride, potassium chloride or magnesium chloride. A preferred salt is sodium chloride.

Since denatured antigen of this invention induces either highly effective oral immune tolerance or stimulation, the administration of the drugs and intake of the functional foods of the invention can inhibit or stimulate immune responses and thus useful for treating and preventing pathogen-caused infections.

For a convenience' sake, in the present specifications the word "oral" includes intranasal, sublingual, bronchial, pulmonary, enteral, parenteral, mucocutaneous, transdermal, and transmucosal in addition to the original meaning of the word "oral".

The oral drugs and functional foods of the present invention contain antigen or plurality of antigens denatured thermally or chemically with the agents specifically and/or inherently associated with a pathogen.

In the present invention, the antigen can be further purified and isolated by conventional methods from raw materials. For example, antigen is prepared by partial digestion of tissues containing antigen with such proteases as pepsin and pronase, and then purification by the differential salting-out method (dialysis). Antigen that is commercially available is also useful. Origins of antigen or tissue containing the antigen are not necessarily restricted. Examples of the origins are as follows; mammals as humans, primates, cattle, pigs, goats, sheep, horses, rabbits, mice, and rats, birds as chicken, turkeys, and ostriches, reptiles as turtles and snakes, and water-living animals like fish, e.g., tuna, bonito, salmon, shark, trout, and ray, shell fish and mollusks; whales and dolphins; insects like shrimp, bees, silk worms, ticks, mosquitoes, and crickets. For example specific avian pathogens are derived from poultry pathogens selected from the group consisting of Newcastle disease virus (NDV), Infectious bronchitis virus (IBV), Infectious bursal disease virus (IBDV), Turkey rhinotracheitis virus (TRTV), Infectious laryngotracheitis virus (ILTV), Egg drop syndrome (EDS) virus, avian encephalomyelitis virus, reticuloendotheleisis virus, avian pox viruses, avian adenoviruses, infectious coryza, fowl typhoid, fowl cholera, *Mycoplasma gallisepticum. E. coli* and *Salmonella.*

Plant infecting pathogens are contemplated as well. Exemplary plant viruses are potexviruses (e.g., PVX), carlaviruses (e.g., PVM), tobraviruses (e.g., TRV, PEBV, PRV), tobamoviruses (e.g., TMV, ToMV, PPMV), luteoviruses (e.g., PLRV), potyviruses (e.g., TEV, PPV, PVY), tombusviruses (e.g., CyRSV), nepoviruses (e.g., GFLV), bromoviruses (e.g., BMV), and topamoviruses. These viruses along with infected tissues are made into fertilizers and are then fed to plants in such manner that allows their absorption into target plant. The compound may also be used against nematodes occurring in the soil or parasitic to plants.

The antigen can be synthesized chemically based on the information about the amino acid or nucleic acid sequences of the antigen of the above-described animal species or by recombinant DNA technology.

For example, an AIDS vaccine can be made comprising a vector which would contain a gag gene, env gene or pol gene of HIV retrovirus under the control of a promoter. The steps in making vector can comprise a step in which a gene fusion is introduced into a host cell, said gene fusion comprising a hybrid DNA molecule which is produced by inserting or fusing the DNA encoding an immunogen into DNA encoding said support and which is fused with a promoter. DNA vector can be derived from a plasmid, a bacteriophage, a virus and/or a cosmid. Viral genes can be assembled together or placed into a vector individually. An exemplary vector can be a live pseudorabies virus, herpes virus, or adenovirus which is able to propagate in a non-complementing cell culture and which produces non-infectious progeny virions, wherein the vector harbors a gene encoding an antigen of a virus not necessarily associated with antibody-dependent enhancement (ADE) of viral infectivity. Other non-infectious, retrovirus-like particles can comprise an assembly of an env gene product, a pol gene product and a gag gene product contain an antigenic marker which is non-retroviral or non-HIV retroviral. In one embodiment, the marker comprises an amino acid sequence containing an epitope inserted into the gag gene product at an antigenically-active insertion site. In another embodiment, the marker comprises an antigenic anchor sequence operatively connected to the env gene product replacing endogenous anchoring function. The non-infectious, retrovirus-like particles have utility in in vivo administration including to humans and in diagnosis. The presence of the antigenic marker enables recognition that antiserum containing anti-retroviral antibodies has been generated by exposure to the non-infectious retrovirus-like particles by testing for antibodies specific to the antigenic marker.

The vector can carry a codon-optimized retroviral, e.g., gag gene, along with a heterologous promoter and transcription terminator. A recombinant vector can also contain nucleic acid sequences of an autonomous parvovirus joined to at least one heterologous nucleic acid sequence. These autonomous parvovirus nucleic acid sequences can comprise functional left and right end inverted terminal repeats, so that heterologous nucleic acid sequence is located between and operably linked to parvovirus nucleic acid sequences comprising left and right inverted terminal repeats, and said vector is in a non-integrating form when transferred into a cell.

In general, recombinant retroviruses carrying a vector construct capable of preventing, inhibiting, stabilizing or reversing infectious, cancerous or auto-immune diseases are desirable. More specifically, the recombinant retroviruses of the present invention are useful for inducing a specific immune response to an antigen or a pathogenic antigen; essentially inhibiting a function of a pathogenic agent, such as a virus; and optionally inhibiting the interaction of an agent with a host cell receptor.

This vaccine can comprise mixtures of at least 1 to about 1,000,000 different recombinant viruses each expressing a different HIV env other viral gene variant or a portion thereof. Such genes can contain both constant and variable regions. These genes and their sequences are readily available from commercial and public nucleic acid and amino acid sequence databases and depositories like GenBank or ATCC, the content of which is incorporated herein by way of reference. Even greater variation can be obtained by substitutions or insertions of at least one nucleotide or one or more amino acid residues, e.g., 1-25 amino acids. For example, the viral proteins are sequence variants of the GP120 protein of HIV which differ from each other in terms of the amino acid sequence in the area of the V2-loop and/or the V3-loop, preferably both the V2- and V3-loop.

Without limiting to above embodiment the oral composition of the invention contemplates a modified form of gp120/160 of HIV-1, said modified form of gp120/160 having a V3 loop disposed thereon, said V3 loop being immunodampened so as to substantially redirect an immune response away from the V3 loop on the modified form of gp120/160 and toward a different part of said modified form of gp120/160. More generally the invention contemplates a modified form of a native antigen of a pathogen, the native antigen having disposed at a position thereon an immunodominant epitope comprising a plurality of amino acids, said modified form of the native antigen having a modified epitope at the position of the immunodominant epitope of the native antigen, said modified epitope having been immunodampened so as to substantially redirect an immune response away from the modified epitope and toward a different part of said modified form of the native antigen.

A genetically engineered cell line is contemplated comprising an nucleic acid sequence encoding an HIV env protein which is then cultured to produce unclipped HIV env protein, which is recovered from the cell culture and prepared according to the process of the invention. Alternatively, oligomeric and glycosylated ectodomains of the surface protein gp160 of HIV as well as the native protein domains themselves are obtained, especially native ectodomains of the env glycoprotein of HIV whose monomers exhibit an electrophoretic mobility of approximately 140 kD. A nucleotide sequence coding for a recognition sequence for protein-splitting enzymes is inserted at a suitable site into the gene coding for the precursor protein of the protein domain to be obtained. After expression of the gene mutant in eukaryotic cells a digestion with a suitable enzyme is carried out and the protein domain to be obtained is subsequently purified.

The composition can also comprise the unprocessed polyprotein initially translated from the genome of a virus and which will contain epitopic configurations that are not retained in the processed proteins. The composition can also contain cryptic epitopes that are not usually "seen" by immune cells in their natural presentation process. The present composition also contemplates a recombinant protein encoding at least two antigenic epitopes joined by flexible hinge domains. In this way the invention is useful as a single vaccine composition effective against diverse infectious agents since the subject proteins can have antigenic epitopes from different infectious agents. Without limitation the composition can contain mimotopes, e.g., a peptide for therapeutic or prophylactic treatment of HIV infection comprising an amino acid sequence or nucleic acid sequence mimicking an antigen conformational epitope of HIV.

As another example a vaccine can comprise a complex of HIV gp120 envelope protein covalently bonded to CD4 or to succinyl concanvalin A or other lectin or hapten. In yet another embodiment the vaccine preparation of the present invention does not contain envelope proteins but contains essentially all other HIV proteins. Such a preparation is either recombinant or prepared by routine standard means by cleaving off envelope proteins and purifying env stripped virions.

Thus a non-infectious immunotherapeutic containing retroviral particles devoid of outer envelope proteins or containing selected antigens isolated from a retrovirus is provided. Once this preparation is obtained one can easily make vaccine preparation according to the preferred scope of the invention. Such a preparation is equally suitable to produce antibodies for passive immunotherapy, alone or in conjunction with active immunotherapy, in individuals infected with a retrovirus, including HIV.

Within the spirit of the invention one can construct a peptide capable of eliciting in a mammal, a neutralizing immune response against a pathogen comprising the steps of: generating a neutralizing antibody specific for an epitope of an antigen of said pathogen, wherein said antigen is a protein or polypeptide; generating an anti-idiotypic antibody specific for said neutralizing antibody; comparing amino acid sequences of said anti-idiotypic antibody and said epitope; identifying an amino acid sequence having at least 6 amino acids of a complementarity determining region of said anti-idiotypic antibody that corresponds to an amino acid sequence of said epitope; synthesizing a peptide which contains said amino acid sequence of said anti-idiotypic antibody that corresponds to an amino acid sequence of said epitope; and administering such a peptide orally. One of specific examples of a peptide eliciting a cytotoxic T lymphocyte response and a high titer neutralizing antibody response is for example a peptide having the following amino acid sequence KQIINMWQEVGKAMYAPPISGQIRRI-HIGPGRAFYTTKN, SEQ ID NO.: 1., which is formulated and administered orally according to the spirit of this invention.

While advantages of above preparation are readily appreciated one can nevertheless obtain an equally suitable composition containing crude gp120 sequentially using ion exchange chromatography, hydrophobic-interaction chromatography, and size exclusion filtration, collecting at each step a fraction that exhibits specific binding affinity for CD4 peptide. The process can be carried out in the absence of any affinity purification steps or any steps (such as reverse-phase HPLC) that use contact protein with organic solvents. The product obtained by this method is a purified, full-length, recombinant or native HIV gp120 glycoprotein having protein/protein interaction properties substantially identical to original gp120 as presented on an HIV virion, including binding affinity for CD4 and binding affinity for at least one antibody capable of neutralizing HIV infectivity.

Without limiting to examples cited supra, synthetic peptides are provided which are advantageous vaccines against HIV. Such peptides comprise an amino acid sequence of a T-cell epitope of the gag protein of HIV, specifically p24 linked directly to an amino acid sequence of a B-cell epitope of the V3 loop protein of an HIV isolate and containing the sequence GPGR, and/or the gp41 containing the sequence ELKDWA. Multimeric forms of the tandem synthetic peptides are equally suitable. Another such peptide can for example have a sequence NH2-lysine-arginine-tryptophan-isoleucine-isoleucine-leucine-glycine-leucine-asparagine-lysine-soleucine-valine-arginine-methionine-tyrosine-cysteine-COOH, which is derived from the gag p24 protein of HIV (i.e. one of the internal core proteins) between residues 263 and 277. Other virus-derived peptides which interact specifically with HLA molecules are equally suitable.

Promoter can be CMV promoter, SV40 promoter, a PGK promoter, vaccinia virus late or early promoter, or TK promoter. The vaccine can further comprise a gene or a gene fragment encoding an unrelated peptide, a polypeptide or a protein belonging to HIV or other virus. A protein can comprise Nef and/or Tat of HIV and an immunostimulatory CpG oligonucleotide. Without limitation an anti HIV vaccine can comprise the entire or part of the Tat HIV 1 protein. The invention can also comprise polyepitopic proteinic fragments of the HIV Nef protein, a method for the production and use thereof.

The vector can also contain polyadenylation signals such as a SV40 polyadenylation signal, a TK polyadenylation signals or an HBV polyadenylation signal. A composition can also contain a post-transcriptional RNA nucleocytoplasmic transport element (NCTE), designated derived from a intracisternal A particle (IAP). The IAP is inserted in a murine osteocalcinrelated gene (ORG) between its promoter and ORG's coding region. Attenuated HIV hybrid virus useful as a vaccine can equally contain a post-transcriptional regulatory element that can function as an RNA nucleo-cytoplasmic transport element. Additionally vector may carry a gene or fragment coding for an interleukin, TNF, GM/CSF, a nonretroviral viral antigen, e.g. gH, gD, gB or gL or a homologue thereof, pertussis toxin, and/or a cancer antigen. Such a viral vector may comprise a recombinant chimeric nucleic acid which is derived from a nucleic acid encoding a fusion partner selected from the group consisting of IL-1, IL-2, IL-4, IL-6, MART-1, gp 10, tyrosinase, bcl-1, bcl-2, c-myc, int-2, hst-1, ras, p53, prostate-specific membrane antigen, papilloma virus protein L1, protein kinase C or G proteins.

A fusion polypeptide can also comprise a chemokine and either a tumor or viral antigen which is administered as either a protein or nucleic acid vaccine to elicit an immune response effective in treating cancer or effective in treating or preventing HIV infection. Also contemplated is a viral regulation protein or a viral regulation protein along with alpha interferon or the alpha interferon fragment which is carboxymethylated.

A live recombinant vaccine for HIV can be constructed using an attenuated strain of *Salmonella* engineered to surface express specific HIV proteins. Two recombinant plasmids, containing the Lpp-OmpA genes required for surface exposure, are followed by the genes for the HIV proteins, reverse transcriptase or transactivating protein (Tat). These plasmids are electroporated into an attenuated strain of *Salmonella* and antigen expression is verified. Such vaccine is then given orally.

In another embodiment a polynucleotide comprising portions of the genomes of caprine arthritis-encephalitis virus and HIV produces a chimeric retrovirus, which is then delivered in a pharmaceutically acceptable carrier.

Other recombinant chimeric viruses are equally suitable including human rhinovirus 14 into which chimeric regions derived from influenza HA, poliovirus or HIV are incorporated. Chimeric human rhinoviruses are particularly advantageous as they are only mildly pathogenic, have numerous potential serotypes and can elicit significant mucosal and serum immunological response.

In yet another embodiment a nucleotide sequence encoding the HIV regulatory protein NEF, REV or TAT or an immunologically active fragment thereof is inserted into a vector comprising papilloma virus nucleotide sequences necessary and sufficient for long-term persistence. The resulting vectors are self-replicating and have a high copy number.

More simple form of vaccine is also feasible having for example essentially pure form of a hydrophilic peptide consisting essentially of an amino acid sequence of about 9 to 35 units in length and corresponding to at least one antigenic determinant of the envelope glycoprotein of HIV recognized by immunocompetent cells, e.g., B lymphocytes, said peptide, when optionally covalently linked to a carrier molecule is administered orally after prepared by the process of the invention.

In case of specifically anti-tumor type vaccine the composition of the invention in addition to denatured tumor cells and lysates thereof can also be enriched with recombinant or naturally derived tumor antigens like MAGE-1, MAGE-3, MEL-1 and peptide fragments thereof; human chorionic gonadotropin and peptide fragments thereof; carcinoembryonic antigen and peptide fragments thereof, alpha fetoprotein and peptide fragments thereof; pancreatic oncofetal antigen and peptide fragments thereof; MUC-1 and peptide fragments thereof, CA 125, CA 15-3, CA 19-9, CA 549, CA 195 and peptide fragments thereof; prostate-specific antigens and peptide fragments thereof; prostate-specific membrane antigen and peptide fragments thereof; squamous cell carcinoma antigen and peptide fragments thereof; ovarian cancer antigen and peptide fragments thereof; pancreas cancer associated antigen and peptide fragments thereof; Her1/neu and peptide fragments thereof; gp-100 and peptide fragments thereof; mutant K-ras proteins and peptide fragments thereof; mutant p53 and peptide fragments thereof; truncated epidermal growth factor receptor, chimeric protein p210BCR-ABL and mixtures thereof.

Thermally denatured antigen of the invention is prepared by heating antigen under neutral, acidic or alkaline conditions. As shown later in examples, such a denaturation treatment results in partial or complete inactivation of pathogen's infectious capacity. The denatured antigen thus obtained can contain partially disinfected pathogen. However, such a pathogen is essentially non-viable, i.e., incapable of replicating itself more than once. For example, a replication-defective HIV particle can be pseudotyped with vesicular stomatitis virus G protein (VSV-G). The pol gene of the HIV genome in the particle is modified to inactivate the pol reverse transcriptase and protease activity. This pseudotyped HIV particle can infect many cell types, including human and simian cells, and only undergoes one round of replication.

For disintegrating for example antigens such as nucleic acids in a biologically active proteinaceous material that preserves its biological integrity one can admix a photodynamic or photoactivatable substance, e.g., phenothiazine or methoxypsoralen, and expose to activating light like laser beam light or ultraviolet light or halogen light so that the nucleic acid content is reduced.

Reduction or process of "reducing" as defined hereinafter comprises a process including rendering, cooking, drying, dehydrating, digesting, evaporating, pulverizing, sonicating, protein concentrating, breaking into small pieces, reducing to powder or granules, blasting, enzyme digestion, dialysis, ultrafiltration, separating by gel migration, and ion exchange chromatography.

While the denaturation of the antigen can sometimes result from reducing process for the purposes of this disclosure the process of denaturing includes heating, treating with a detergent, oxidizing, aldehyde treatment, subjecting to extreme pH conditions like acid or alkaline treatment, the preferred means are however the thermal denaturation.

Although the conditions for the thermal denaturation may vary depending on the heating temperature and period, heating for longer than 10 min at a temperature higher than 60° C. is usually adopted. Furthermore, heating for longer than 15 min at a temperature higher than 65° C. is preferable, and an autoclave is even more preferable, e.g., heating for about 20 minutes or more at 110° C. or higher.

Thermal denaturation can be accompanied by acid and base treatments. To provide acidic conditions, organic or inorganic acid solutions are useful; e.g., citric, acetic, carbonic acid, or hydrochloric acids. The pH range is preferably below 5.5 and more preferably between 1.0 and 4.5. To provide alkaline conditions, organic or inorganic alkali solutions are useful; e.g., sodium hydroxide, potassium hydroxide, and triethanolamine. The pH range is preferably above 8.5 and more preferably between 9.5 and 12.0.

The typical thermal denaturation conditions can be also accompanied by pH conditions between 2.0 and 4.5 or between 10.0 and 12.0, at a temperature between 100 and 120° C., for a period between 10 and 15 minutes. In another embodiment, the thermal denaturation conditions are heating antigen in an inorganic or organic acid solution for longer than 15 min or preferably for longer than 20 min at above 65° C. or more preferably at about 100° C., or heating in an autoclave for longer than 30 min or preferably for 2 to 10 h at about 110° C., or for longer than 15 min or preferably for 20 min or longer at about 120° C.

Products containing thermally denatured antigen (e.g., soup) can also be prepared by hot-water extraction of raw materials containing antigen, e.g., cartilage of joints of sick animals.

The present inventor considers that the denaturation treatments by heat or with the agents reduces the molecular weight of antigen and destroys its steric molecular structure, and that denatured antigen having the destructed helical structure is safer causing less side effects than does native antigen. According to another embodiment the three-dimensional structure of the antigen is essentially intact.

It is not important that denaturation step follows immediately the reduction step. For example, reduced antigen and tissue can be formulated in the final product, e.g., functional food-like meat products and fish products, dairy products like milk or cheese, beverages like juice, milk, and tea, and liquid or solid drugs and only then pasteurized or denatured.

Liquid compositions can contain conventional additives such as suspending agents, for example sorbitol syrup, methyl cellulose, glucose/sugar syrup, gelatin, hydroxymethylcellulose, carboxymethylcellulose, aluminium stearate gel or hydrogenated edible fats; emulsifying agents, for example lecithin, sorbitan monooleate or acacia; non-aqueous vehicles, which can include edible oils, for example vegetable oils such as arachis oil, almond oil, fractionated coconut oil, fish-liver oils, oily esters such as polysorbate 80, propylene glycol, or ethyl alcohol; and preservatives, for example methyl or propyl p-hydroxybenzoates or sorbic acid. Liquid compositions may conveniently be encapsulated in, for example, gelatin to give a product in dosage unit form.

The reduced and denatured antigen can be eaten as foods or as a food additive with or without enrichment with various nutrients or dispersion in beverages to treat and prevent pathogen infection. After adding the appropriate carriers and additives according to the conventional practices, the functional foods may be formed in shapes and forms suitable for eating (e.g., granule, grain, tablet, capsule, and paste), added to various solid foods, e.g., such meat products as hams and sausages, fish products, candies, chocolate, candy bars, chewing gums, flour, flakes, bread, milk powder, breast-milk formulas, and butter, and various liquid or semi-solid foods (potable water, jam, juice, milk, wine, beer, purees, infant foods, ice-cream, and soft drinks). For example, denatured composition and natural juice can be blend at desired ratio, e.g., 0.5 mg to 200 ml, sterilized conventionally and packaged aseptically to obtain a juice product.

The dosage of denatured antigen formulated in various functional foods may properly be adjusted depending on the age, body weight, severity, degrees of the disease of the patient, and shape of the food. The dose of the antigen may range between 0.0005 microgram/kg and 15 g/kg of body weight/day. Intake of more or less than those dosages, however, is harmless, since denatured antigen has no harmful effect on living bodies, even if a large amount is taken.

The active component of denatured antigen can be blended with solid or liquid pharmaceutical carriers prepared in various pharmaceutical forms and administered. Dosage forms can include pharmaceutically acceptable carriers and adjuvants which are known to those of skill in the art.

An exemplary adjuvant composition of an oil-in-water submicron emulsion may consist essentially of about 0.5 to 50% of a first component of an oil, about 0.1 to 10% of a second component of an emulsifier, wherein the emulsifier is a phospholipid compound or a mixture of phospholipids selected from the group consisting of phosphatidylcholine, phosphatidylethanolamine, phosphatidylserine, phosphatidylinositol, phosphatidylglycerol, phosphatidic acid, sphingomyelin and cardiolipin, about 0.05 to 5% of a non-ionic surfactant, about 0.00001, to 10% of an immunogen of the invention, and an aqueous continuous phase. This submicron emulsion can have a mean droplet size in the range of between about 0.03 and 0.5 micrometer.

Another exemplary adjuvant can contain one or more adjuvants/vehicles like polyoxyethylene sorbitan monoesters, polyoxyethylene castor oil, caprylic/capric acid glycerides and gangliosides in an amount of about 0.01 to 45% (v/v) calculated on the total volume of the preparation.

Other typical carriers and adjuvants include, for example, ion exchangers, alumina, aluminum stearate, lecithin, serum proteins, such as human serum albumin, chitosan, buffer substances such as phosphates, glycine, sorbic acid, potassium sorbate, partial glyceride mixtures of saturated vegetable fatty acids, one or more saponin-lipophile conjugates, desacylsaponin, triterpene saponins, saponarin, sarmentocymarin, sapogenins, sarmentogenin, sarsasapogenin, sarverogenin, N-palmitoyl-S-2,3(bispalmitoyloxy)-propylcysteinyl-seryl-serine, an unsaturated turpin hydrocarbon, like squalene or squalane, a polyoxypropylene-polyoxyethylene block copolymer, anionic lipids like salts of lauric and oleic acids, lauric and oleic acids, acid esters of lauryl and cetyl alcohol, and sulfonates, lectins, estrogenic compounds, a peptide to which has been attached a hydrophobic tail, said peptide being adsorbed to viral particles comprising intact virus surface antigen attached via said hydrophobic tail, a synthetic peptide carrier which may constitute a T cell epitope, e.g., one derived from the which corresponds to positions 437-453 of *E. coli* hsp65 (GroEL), or an analog thereof, cyclic peptides containing as constituting strand(s) one or two amino acid sequences selected from among amino acid sequences Glu-Ala-Asp-Asp-Arg and/or Ser-Gln-Lys-Glu-Gly, peptide having the amino acid sequence X-Ser-Ser-Ser-Gly-Arg-Met-Ile-Met-Glu-Lys-Gly-Glu-Ile-Lys-Asn-Cys-Ser-Phe-Asn-Ile-Ser-Thr-Ser-Y wherein X is either a hydrogen atom of the amino terminal NH2 group of said peptide or an additional amino acid selected to facilitate coupling of said peptide to a carrier and Y is selected from the group consisting of an amino group, hydroxy group, cysteine residue, cysteine residue followed by an amino group and cysteine residue followed by a hydroxy group, hemagglutinin protein, BCG, diphtheria, tetanus, whole cell pertussis, polio, hepatitis B, *hemophilus influenza*, measles, mumps and rubella immunogens, or any other viral, fungal, bacterial, protozoan or parasite protein/immunogen that in combination can elicit desired immune response, hydroxylated lower alkyls, dimethyl sulfoxide, urea, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances and polyethylene glycol. Adjuvants for topical or gel base forms of the compounds and compositions of this invention include, but are not limited to, sodium carboxymethylcellulose, polyacrylates, waxes, polyoxyethylene-polyoxypropylene-block polymers, polyethylene glycol, propylene glycol and wool fat.

A pharmaceutically acceptable salt is a salt that retains the biological effectiveness and properties of the active ingredient of the composition and which is not biologically or otherwise undesirable. The present composition can be provided in form of a salt. Salts can be derived from acids or bases. The acid addition salts can be derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, and the like. The base addition salts can be derived from inorganic bases, and include sodium, potassium, lithium, ammonium, calcium, magnesium salts, and the like. Salts derived from organic bases include those formed from primary, secondary and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like. Preferred organic bases are isopropylamine, diethylamine, ethanolamine, piperidine, tromethamine, and choline.

Compositions for topical administration include ointments, creams, gels, lotions, shampoos, paints, powders (including spray powders), pessaries, tampons, sprays, dips, aerosols, pour-ons and drops. Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically-acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.001 to 10 micrometers. The active ingredient can, for example, be formulated in a hydrophilic or hydrophobic base as appropriate.

The aerosol type agent can be prepared generally by providing a sterilized solution or suspension containing the effective ingredient and then adding a propellant thereto. In preparing the solution or suspension, there can be used all diluents commonly used in the art, such as those mentioned with respect to the injection. As to the propellant, there can be used all propellants commonly used in the art, such as liquefied gas propellants for example, chlorofluorocarbons (e.g., Flon 12 or Flon 123), compressed gas propellants (e.g., nitrogen gas and carbon dioxide) and the like. The aerosol type agent may further contain a solubilizing agent, a buffer solution, etc., which are used commonly and, if necessary, the aerosol type agent may contain a coloring agent, a preservative, a perfume, a flavoring agent, a sweetening agent, etc.

Examples of oral pharmaceutical forms are, e.g., solid drugs as tablet, granule, powder, and capsule, such liquid ones as solution, suspension, and emulsion, and lyophilized one, inhalants, skin patches, bolus pumps, controlled release devices, suppositories, and trans-intestinal liquid. These drugs can be prepared by conventional pharmaceutical practices. Examples of the above-described pharmaceutical carriers are glucose, lactose, sucrose, starch, mannitol, dextrin, fatty-acid glyceride, polyethylene glycol, hydroxyethyl starch, ethylene glycol, polyoxyethylene sorbitan fatty-acid ester, amino acids, albumin, water, and physiological saline. Furthermore, such conventional additives as stabilizer, smoother, humectant, emulsifier, and caking agent can be added. Tablets and capsules according to the invention can, if desired, contain conventional ingredients such as binding agents, for example syrup, acacia, gelatin, sorbitol, tragacanth or polyvinyl-pyrollidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. Tablets can be coated according to methods well known in the art.

In shaping the external preparation like tablets and pills, there can be used various materials known in the art. As the base, for example, there can be used at least one base selected from various oily bases or various water-soluble bases. Specific examples of the base are oils and fats such as peanut oil, sesame oil, soybean oil, safflower oil, avocado oil, sunflower oil, corn oil, rape seed oil, castor oil, camellia oil, coconut oil, olive oil, poppy seed oil, cacao oil, beef tallow, lard, and the like; modified oils and fats obtained by subjecting the above-mentioned oils and fats to chemical treatments (e.g. hydrogenation); mineral oils such as petrolatum, paraffin, silicone oil, squalane and the like; higher fatty acid esters, higher aliphatic alcohols and waxes such as isopropyl myristate, N-butyl myristate, isopropyl linoleate, propyl ricinoleate, isopropyl ricinoleate, isobutyl ricinoleate, heptyl ricinoleate, diethyl sebacate, diisopropyl adipate, cetyl alcohol, stearyl alcohol, bleached bees wax, spermaceti, Japan wax, hydrous lanolin, carnauba wax, shellac wax and the like; higher fatty acids such as stearic acid, oleic acid, palmitic acid and the like; mixtures of mono-, di- and tri-glycerides of saturated or unsaturated fatty acids of 12-18 carbon atoms; polyhydric alcohols such as ethylene glycol, polyethylene glycol, propylene glycol, polypropylene glycol, glycerin, batyl alcohol, pentaerythritol, sorbitol, mannitol and the like; gummy substances such as acacia, gum benzoin, guaiacum, tragacanth gum and the like; natural water-soluble polymers such as gelatin, starch, casein, dextrin, pectin, sodium pectate, sodium alginate, methyl cellulose, ethyl cellulose, carboxymethyl cellulose, hydroxyethyl cellulose, hydroxypropyl cellulose, nitrocellulose, crystalline cellulose and the like; synthetic water-soluble polymers such as polyvinyl alcohol, polyvinyl methyl ether, polyvinylpyrrolidone, sodium polyacrylate, carboxyvinyl polymer, polyethyleneimine and the like; nonionic, anionic or cationic or amphoteric surfactants; ethanol; isopropanol; and water. In the present invention, these bases can be used singly or in admixture of two or more.

Generally, according to the invention any infected tissue as a starting material is adequate and suitable. The preferred embodiment of the invention is blood. Blood is collected, preferably from donors already infected with the pathogen. According to this embodiment, the blood can be held with anticoagulants such as sodium citrate or EDTA to prevent clotting. Prevention of clotting is not essential to the invention. Typically, the whole blood is separated, preferably by centrifugation, although any other separation method may be used, into two parts, the cellular solid material (red cells, white cells, platelets, and other circulating cells or precursors thereof) and liquid form like plasma or serum. As used herein the term "plasma" shall include the serum and plasma portion of blood as well as any of the protein and components which may be further purified therefrom. Plasma and/or the purified components of plasma, may then be further concentrated (by membrane filtration). The blood is next dried to form a beige/brown powdery substance. When this powder is washed and dried again it results in white crystalline powder. The resulting powdery substance can have a particle size of about 0.5 to about 30 microns or higher. Optionally, the powder can be further compacted or compressed (around 1200 to 1400 psi) to form granules and screened or otherwise separated by size to increase homogeneity. The resulting granulated particle size is at least about 50 microns. Preferably the size is greater than about 100 microns in diameter. The resulting granular substance can then be combined with other ingredients for any desired therapeutic regimen or may be blended with an ingredient and the blend granulated. The granulated blended composition preferably comprises from greater than 0 to about 50% by weight of the base product.

The composition of the invention can be admixed with a natural polymer like starch, dextran, dextrin, and maltodextrin or a hydrolysate of a natural polymer, or a mixture thereof. Natural polymer can be a cross-linked polysaccharide, a cross-linked oligosaccharide, a derivative or hydrolysate of a cross-linked polysaccharidec or a cross-linked oligosaccharide, and a mixture thereof. The core containing the composition can be uncoated, or is partially or completely coated with no more than one layer, the layer comprising a lipid compound covalently bonded to the core, or an amphiphilic compound.

In addition to granulation, many methods, such as pelleting, wet or dry agglomeration, prilling, and fluid-bed drying, can be used to modify as desired the particle size and density of dried blood or plasma and/or its component proteins and are included within the scope of the invention.

According to another embodiment of the present invention, the blood composition is obtained from animal sources, granulated and fed with other feed ingredients to domestic animals, which need intervention against pathogen infection. Any animal in which it is desirable to prevent or treat infection, can be fed the composition according to the invention. These animals include but are not limited to cats, dogs, cows, sheep, pigs, chicken, turkeys, ducks, horses, donkeys, camels, goats or aquaculture. Wild animals in need of treatment or prevention are also contemplated as targets of intervention.

The composition is obtained by collecting blood from pathogen-infected animals. Infection can be natural or deliberate to create starting material for the composition. Naturally infected blood, which is traditionally discarded, can be used for preparation of the compositions and implementation of methods of the invention.

In further aspects, methods are provided for administering any of the above-described composition, for a prophylactic or therapeutic effect. For example, within one aspect, the present invention provides methods of stimulating or inhibiting an immune response to an antigen or modified form thereof being capable of modulating an immune response within an animal.

In another embodiment, the cells of a healthy animal are removed, infected ex vivo by a pathogen, made into a composition and returned to the animal via mucosal surface, e.g., orally. In yet another embodiment, tissues and pathogen from a sick animal are processed according to this instant process and fed back to the same animal.

The specific therapeutically effective doses for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved. This is a routine clinical procedure that does not require the undue experimentation. Generally, the total daily dose of the compounds of this invention administered to a human or lower animal may range from about 0.001 to about 100 mg/kg of patients body mass/day. For purposes of oral administration, more preferable doses may be in the range of from about 0.005 to about 30 mg/kg/day. If desired, the effective daily dose may be divided into multiple doses for purposes of administration; consequently, single dose compositions may contain such amounts or submultiples thereof to make up the daily dose. If necessary, the composition can be given in less frequent regimen, e.g., once every 3 days, once weekly, once monthly, once every 3 months, or once every 6 months as needed. Doses given once a year or less frequently as required by exigencies of the therapy or patient's condition are also contemplated as equally suitable. In general, the therapy can be administered as often as necessary and for the duration of time deemed necessary. An effective amount means that amount necessary to delay the onset of, inhibit the progression of, halt altogether the onset or progression of or diagnose the particular condition being treated. In general, an effective amount for treating for example cancer will be that amount required to inhibit mammalian cancer cell proliferation in-situ either directly or indirectly via recruitment of immune cells. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that an optimal dose be used, that is, the safest and the most potent dose according to sound medical judgment.

Dosage may be adjusted appropriately to achieve desired drug levels, locally or systemically. Generally, daily oral doses of active compounds will be from about 0.0001 mg/kg per day to 1000 mg/kg per day. Preferably the systemic levels of the composition are within the same range as shown effective in an in vitro and animal models. It is expected that injectable doses in the range of about 1 to 1000 mg/m$^2$ per day will be effective and the optimal dosage is determined by a routine pharmacokinetic, dosage-scaling experimentation well within the skill of the practitioner. In the event that the response in a subject is insufficient at such doses, even higher doses (or effective higher doses by a different, more localized delivery route) can be employed to the extent that patient tolerance permits. Continuous dosing over, for example 24 hours or multiple doses per day are contemplated to achieve appropriate systemic levels of compounds.

The preventive and therapeutic methods described herein can be used alone or in conjunction with additional therapy known to those skilled in the art for the treatment of a given disease or condition. The pharmaceutical composition of the present invention can also comprise other active agents or drugs. In yet another embodiment, the composition can be administered in combination with other drugs or pharmaceutically active ingredients including but not limited to vitamins, anthracycline, i.e., doxorubicin, 4'-epi-doxorubicin, 4- or 4'-deoxydoxorubicin, etoposide, epothilone A-C, N-bis(2-chloroethyl)-4-hydroxyaniline, 4-hydroxycyclophosphamide, vindesine, vinblastine, vincristine, terfenadine, terbutaline, fenoterol, salbutamol, muscarine, oxyphenbutazone, salicylic acid, p-aminosalicylic acid, 5-fluorouracil, methotrexate, diclofenac, flufenamic acid, 4-methylaminophenazone, theophylline, nifedipine, mitomycin C, mitoxantrone, camptothecin and camptothecin derivatives, N-[4-(9-acridinylamino)-3-methoxy-phenyl]-methansulfonamide ("m-AMSA"), taxol or other taxanes, nocodaxol, colchicine, fexofenadine, cyclophosphamide, rachelmycin, cisplatin, melphalan, bleomycin, nitrogen mustard gas, phosphoramide mustard gas, verrucarin A, neocarcinostatin, calicheamicin, dynemicin, esperamicin A, quercetin, genistein, erbstatin, tyrphostin, rohitukin derivative, retinoleic acid, butyric acid, phorbol ester, dimethyl sulfoxide, aclacinomycin, progesterone, buserelin, tamoxifen, mifepristone, onapristone, N-(4-aminobutyl)-5-chloro-2-naphthalenesulfonamide, pyridinyloxazol-2-one, quinolyl- or isoquinolyloxazol-2-one, staurosporin, ethanolamine, verapamil, forskolin, 1,9-dideoxyforskolin, quinine, quinidine, reserpine, 18-O-(3,5-dimethoxy-4-hydroxybenzoyl)-reserpate, lonidamine, buthionine sulfoximine, diethyl dithiocarbamate, cyclosporin A, rapamycin, azathioprine, chlorambucil, hydroxycrotonamide derivative 2, leflunomide, 15-deoxyspergualine, FK 506, ibuprofen, indomethacin, aspirin, sulfasalazine, penicillamine, chloroquine, dexamethasone, prednisolone, mefonamidic acid, acemannan, acetaminophen or paracetamol, 4-aminophenazone, chloroquine, amodiaquin, hydroxychloroquine, primaquine, quinacrine muskosine, orciprenaline, isoprenaniline, thalidomide, linomide, amiloride, p-nitrophenyl guanidine benzoate, 1,25-dihydroxy Vitamin D3, biologically active Vitamin D3 derivatives, all trans-retinoic acid, retinoic acid derivatives, retinol, retinol derivatives, glucocorticoids, dehydroepiandrosterone (DHEA), DHEA-derivatives like DHEA-sulfate (DHEA-S), 16-alpha-bromo-DHEA, 7-oxo-DHEA, 16-alpha-Br-DHEA-S, 7-oxo-DHEA-S or their derivatives in which one or more hydroxyl, amino or imino groups have been additionally substituted. Other drugs contemplated in this invention can be readily glanced from public databases like http://pharminfo.com/drugdb/db_nmu.html; www.rxlist.com; http://www.medicineinfo.com; www.phrma.org; www.aphanet.org; www.pjb-pubs.co.uk; www.drugbase.co.za; http://www.prescript.com; or http://www.musclerelaxant-medications.com/index1.htm incorporated herein by way of reference. These active compounds belong to various classes of drugs like antitumor agents, standard cytostatics, antimetabolites, substances that intercalate DNA, inhibitors of topoisomerases, tubulin inhibitors, alkylating agents, compounds that inactivate ribosomes, tyrosine phosphokinase inhibitors, differentiation inducers, hormones, hormone agonists or hormone antagonists, substances which modify the pleiotropic resistance to cytostatics, calmodulin inhibitors, protein kinase C inhibitors, G protein receptor antagonists, cell cycle-related molecule antagonists, P-glycoprotein inhibitors, modulators of mitochondrially bound hexokinase, inhibitors of gamma-glutamylcysteine synthetase or of glutathione S-transferase, inhibitors of superoxide dismutase, inhibitors of the proliferation-associated protein in the cell nucleus of dividing cells, substances which exert immunosuppressant effects, standard immunosuppressants, macrolides, nonsteroidal antiinflammatory substances, antirheumatic drugs, steroids, antiinflammatory, analgesic or antipyretic substances, antiviral drugs, antibiotics, derivatives of an organic acid, nonacidic analgesics or antiinflammatories, local anesthetics, medicinal herbs and plants, antiarrhythmics, $Ca^{++}$ antagonists, antihistaminics, phosphodiesterase inhibitors, parasympathomimetics, sympathomimetics or substances having inhibitory action on human urokinases among many others.

The following examples serve to illustrate the invention and are not intended to limit the invention in any way. Those skilled in the art will recognize that there are several different parameters which may be altered using routine experimentation and which are intended to be within the scope of this invention.

EXAMPLES

Example 1

Carbon Dioxide Process

Whole blood or blood serum or plasma or cell culture medium with pathogen-infected cells present in them are treated with carbon dioxide ($CO_2$) in a pressurized vessel and heated. Other common gases like ozone, oxygen, nitric oxide (NO); liquid nitrogen, and mixtures thereof can be equally used.

Under these conditions, $CO_2$ reacts with the moisture in the vessel to form a weak acid. The combination of acid and heat causes the ingredients such as cells and proteins to form two fractions, one a solid and the other a liquid. The solid fraction is of interest for use in making instant composition. The liquid fraction is also useful since it contains cell-free pathogen. To separate the fractions, two different methods are equally suitable: centrifugation and membrane separation. In centrifugation, the mixture of the fractions is placed in a container and spun at a high rate of speed so that the heavier solid fraction settled to the bottom of the container. The liquid fraction is decanted off and further processed. In membrane filtration, the mixture of the fractions is pumped past or poured over a porous membrane. The fractions are separated easily because the liquid fraction passes through the pores of the membrane leaving a concentrated solid on the surface of the filter. Both methods are equivalent in recovery of the proteins and solid matter. The solid matter can be further processed, e.g., autoclaved, made into a powder, and compounded into granules or tablets. These steps can be in any order.

The additional advantage of gas treatment is provided by explosion or bursting of the target antigen by gas bubbles into smaller fragments, effectively reducing the initial size. The reduced form is inherently the part of the body of antigen. According to one of embodiments the reduced antigen keeps its physical structure and shape such as their molecular and supramolecular curve and cleft close to the initial three-dimensional form as much as possible. According to another embodiment the reduced form is at variation with the initial structure. In yet another embodiment the original monodisperse colloids and crystals of the composition are effectively converted into hollow shapes pretty much as in "lost-wax" approach. These are encased in the pharmaceutical carrier and formulated as an oral pill. Upon digestion in the gut the carrier releases the original parts or fragments of an antigen and presents it to the immune system of a host when it is processed via usual cellular pathways, e.g., antigen presentation via MHC Class 1 or 2 by specialized mucosal (regular enterocyte, Peyer's patch cell or M cell) and/or perimucosal dendritic cells residing in mesenteric lymph nodes or in Peyer's patch and functioning as antigen presenting cells (APC). The vaccine protein or polypeptide which is either natural or recombinant can thus comprise, for example, the alpha-3 domain of a MHC class 1 molecule, a membrane-anchoring structure and an antigenic polypeptide determinant. This antigenic polypeptide determinant can substitute either a portion of the alpha-1, alpha-2 or both the alpha-1 and alpha-2 domains of MHC class 1 molecule, wherein said polypeptide vaccine is expressed in membrane-bound form on the surface of a cell and wherein said antigenic polypeptide determinant is capable of interaction with T-lymphocyte receptor.

Equipment used for this and other reduction and denaturation processes are commercially available. One skilled in the art can easily select appropriate ones among Rotary Drums, Sectional Coolers, (Drying and Cooling) Flash Dryers, Fluidized Bed Plants, Turbo-Tray Dryers, Solidizer, Disc Dryers, Spirocorn, Belt Dryers, Tray Dryers Simplicior and Favorit, Air Mix, Spray Mix, Mills and Classifiers and order them from various manufacturers like Duske Engineering, Inc. Fenwal, Baxter, among many others.

Example 2

Freeze-Drying Process

The prior art method for freeze-drying or lyophilization is well established, for example, in Remington's Pharmaceutical Sciences, 18th Edition, Mack Publishing Company, Easton, Pa., U.S.A., or in U.S. Pat. No. 4,001,944.

This method uses a vacuum chamber and a condenser. The aqueous product contained in bottles or tissue blocks are frozen in an inert atmosphere at a temperature below its eutectic temperature; the samples are supported on a refrigerated shelf in the chamber. The chamber is evacuated usually below 0.1 Torr (100 microns of mercury pressure). The ice which is produced is then sublimed from the product onto the condenser at a temperature below that of the product. Finally, heat is introduced to the product by warming the shelf to provide energy for sublimation while keeping the product below its eutectic temperature.

TABLE 1

Typical amino acid profile of blood-derived composition (%)

| | |
|---|---|
| Crude protein | 86 |
| Arginine | 3.6 |
| Histidine | 5.2 |
| Isoleucine | 0.9 |
| Lysine | 7.5 |
| Methionine | 1.0 |
| Threonine | 3.6 |
| Tryptophan | 1.0 |
| Valine | 7.5 |

Example 3

Spray Drying Process

The process described below is for whole blood but can be easily carried out with any blood cell fraction or cell culture instead. The process is preferably carried out in an assembly of apparatuses comprising a container with indirect steam heating, a container with direct steam heating and a feeding screw, a centrifuge, a grinding equipment, an autoclave with a supply of steam, a second centrifuge, an evaporation equipment, a spray drier, a mixing vessel, and an optional second spray drier. These apparatuses can be interconnected so that the process is automated and involves limited operator involvement. For the sake of convenience, the quantities given below are based on the processing of 1 liter or 1 kg of raw blood. One kg of whole blood with a dry matter content of about 16% by weight is fed into the first container and heated to 30-40° C. by introduction of steam into the jacket of the container. After remaining in the container for one hour, the blood is fed to a second container, where it is heated to 95-98° C. by blowing in steam. After the blood has coagulated, it is fed to a centrifuge, where it is separated into a water phase and a solid phase. The maturation process preceding the coagulation takes place at a slightly raised temperature, and has the effect of minimizing the loss of protein with the water phase leaving the centrifuge, the protein content of this water phase is preferably less than about 1% by weight. The major part of the salts in the whole blood (including the anticoagulant citrate used during blood collecting) is contained in the water phase, which can be discarded. The solid phase leaving the centrifuge can be as low as 0.15 kg dry matter and 0.225 kg water. Thus, the dry matter content is approximately 40% by weight. The solid phase can be diluted with water to a dry material content of about 25% by weight, and then is fed to the grinding equipment. The grinding serves to create the greatest possible surface area for the subsequent hydrolysis process and prevents agglomeration of the coagulated blood particles. After grinding, the solid phase is transferred to the pressure container. The solid phase is heated in the container by directly blowing in pressurized steam, and it is hydrolyzed at a pressure of approximately 600-800 kPa (6-8 bar) and a temperature of 120-170° C. for about 10-60 minutes. During hydrolysis, some of the amino acid links in the protein are broken, which results in short-chain, water soluble peptides. After the hydrolysis process, the hydrolyzed blood mass is fed to the centrifuge or to an ultrafiltration equipment, in which the mass is separated into a liquid phase containing soluble peptides, and a solid phase containing non-hydrolyzed protein. The solid phase, which contains about 40% by weight of dry matter, is diluted to a solid content of about 25% by weight in the mixing vessel, and is then spray-dried in the spray drier at appropriate temperature. In a spray drying machine it is preferable that inlet temperature is approximately 375 to 400° F. and an outlet temperature from the drier of 180-200° F. This yields a blood powder as a final product. The liquid phase, which contains less than 16% by weight of dry matter, is evaporated in the evaporation equipment to a dry matter content of 35-40% by weight. The concentrate is then fed to the spray drier and spray-dried to a fine powder. The mixture of two blood powders obtained by the spray-drying process is light brown and slightly bitter tasting. It contains about 90% of raw or total protein by weight; fat or lipids at about 0.3%; ashes about 5%; iron about 360 mg/kg and water about 5%. Spray-dried plasma powder is obtained by a similar process. The obtained powder is able to pass through a 12 mesh screen and is collected on a 30 mesh screen. In addition, spray dried animal plasma is commercially available from several sources including American Meat Protein Corporation product sold under the mark of AP920 and can be added to instant powder as a "bulking" additive, especially in case of a composition made out of cell cultures.

An optional granulation of powder is equally suitable and desirable. Granulation has long been used to improve flowability of fine hygroscopic powders and ease of handling.

It is also expected that granulation would beneficially affect the clinical efficacy, beyond simply what is observed for similar amounts of powder. While granulation step is well known to those of skill in the art a typical compaction/granulation system for use in the present invention consists of following. Normally, the powder leaves the powder feed and advances through a screw wherein the powder is pre-compressed and acerated. The pre-compressed powder then enters a compaction chamber containing compaction rolls. Therein, a hydraulic actuator regulates the amount of pressure exerted on the rolls. From the compacting chamber, the compressed material enters a grinding mill and thereafter passes through a screen wherein the granules are screened to the desired size. The granular product of appropriate particle size is then gathered. The "overs" are recycled with the "fines" from the process through the recycle system or may be recycled through the grinding mill wherein the granulation process is repeated. The granular product is then stored in moisture-resistant containers. Without being limited to particular doses and ranges the representative chemical and other properties of the composition include about 60-90% protein, about 5-9% moisture, about 5-20% ash, about 1-5% fat, iron, calcium, chloride, phosphorous, potassium, and other ingredients inherently present in original raw material. A typical amino acid assay of the powder by acid hydrolysis and subsequent column chromatography results in the following amino acid concentrations (grams per 100 grams of powder):

TABLE 2

The composition of three representative batches (%)

Batch #1

| | |
|---|---|
| Crude protein | 50 |
| Cystine | 0.3 |
| Methionine | 0.9 |
| Aspartic acid | 11.2 |
| Threonine | 3.9 |
| Serine | 5.1 |
| Glutamic acid | 10.6 |
| Proline | 4.1 |
| Glycine | 5.1 |
| Alanine | 8.5 |
| Valine | 9.1 |
| Isoleucine | 1.0 |
| Leucine | 12.1 |
| Phenylalanine | 5.9 |
| Histidine | 6.2 |
| Lysine | 8.9 |
| Arginine | 3.7 |
| Tryptophan | 1.9 |

Batch #2

| | |
|---|---|
| Crude protein | 60 |
| Alanine | 4.2 |
| Arginine | 4.7 |
| Aspartic Acid | 7.9 |
| Cystine | 2.8 |
| Glutamic Acid | 11.7 |
| Glycine | 3.0 |
| Histidine | 2.8 |
| Isoleucine | 2.9 |
| Leucine | 7.8 |
| Lysine | 6.8 |
| Methionine | 0.7 |
| Phenylalanine | 4.6 |
| Proline | 12.8 |
| Serine | 4.7 |
| Threonine | 4.8 |
| Tryptophan | 1.4 |
| Tyrosine | 3.6 |
| Valine | 6.3 |

TABLE 2-continued

The composition of three representative batches (%)

Batch #3

| | |
|---|---|
| Crude Protein | 78 |
| Isoleucine | 2.3 |
| Lysine | 7.4 |
| Methionine | 2.4 |
| Threonine | 4.2 |
| Tryptophan | 1.2 |

Example 4

Preparation of White Powder

A number of additional steps can be carried out to further modify the composition as desired. For example, to obtain a product having higher whiteness degree one can adopt the procedures well known in the art as disclosed in Japanese patent JP1988000041437 and/or U.S. Pat. No. 4,262,022. Accordingly, whole blood, blood before separation, erythrocyte, hemoglobin or a dried substance thereof is diluted with an alcohol or an aqueous solution of an alcohol (e.g., about 2.5 to 5 times dilution ratio of solid content at about 40% alcohol concentration), adjusted to pH around 1.5 to 5.5, preferably 2 to 5, incorporated with 0.05 to 0.6 the solid content weight of a chlorite and heated at 40 to 65° C. to discolor hemoglobin or hemoglobin-containing blood. Another process for producing a decolorized edible material from blood is achieved by hemolyzing a red blood corpuscle containing blood fraction; then partially hydrolyzing the hemolyzed blood fraction enzymatically with the proteinase of *Bacillus licheniformis* to a degree of hydrolysis of at least 10, forming a hydrolyzate constituted of a decolorized supernatant containing partially hydrolyzed protein dissolved therein and a sludge; and thereafter deactivating the proteinase and recovering the supernatant.

While these steps are suitable one skilled in the art can simply proceed with a repeated washing steps with simple solvent such as distilled water until the baked brownish powder becomes white in appearance.

Example 5

Composition Other Than Powder

This invention also provides a process for preparing non powdered product comprising: reacting muscle cells or blood with a nitrosating agent and a reductant, at elevated temperatures, to provide a cooked cured-meat-like product; stabilizing and/or encapsulating and/or protecting the cooked cured-meat, to provide a stabilized cooked cured-meat; and drying the stabilized cooked cured-meat by spray-drying, drum-drying or freeze-drying techniques. This invention also provides the combination of an emulsion-type meat or fish product with a cooked cured-meat and a nitrosating agent, in stabilized, encapsulated or protected form. A composition containing water is also contemplated having dispersed therein a nucleic acid or peptide or a plurality of active peptides or oligonucleotides each of which consists essentially of 2 to about 500 residues having a sequence that corresponds to a portion of a conserved domain of an HIV protein or genome, said composition, when used to immunize an animal, having the capacity to induce cell-mediated immune activation as well as inducing humoral immune reaction, i.e., antibodies, that immunoreact with said corresponding native HIV.

Example 6

Sodium Hydroxide and Acid Hydrolysis by pH Adjustment

Bovine blood cells (10 g) are added to 90 mL of 8:1 (v/v) distilled water/sodium hydroxide containing reductant(s) into which a nitrosating agent is introduced. Reducing agents (ascorbic acid, erythorbic acid, and/or ascorbyl palmitate) are added to the reaction mixture at a heme in RBC to reductant mole ratio of 1:5, 1:10, or 1:20. Sodium nitrite, the nitrosating agent employed, is added at a molar ratio of 1:10, heme to nitrite. The reaction mixture is heated at about 85° C. (lower temperatures of 75° and 80° C. are also acceptable) for 15 min with intermittent stirring, cooled in an ice bath to room temperature, and centrifuged for 2 min at 3000 rpm. The supernatant is acidified to pH 4 with 0.1M citric acid. Acidification can also be performed before cooling and centrifugation. Use of acetic (0.1 M), hydrochloric (0.1 M), phosphoric (0.2 M) or sulfuric (0.05 M) acids as acidifying agents is also suitable. During acidification solubilized proteins are precipitated. After centrifugation for 2 min at 3000 rpm (905×g), supernatant containing residual nitrite from the process is discarded. Yield and purity of product obtained from heat-treated cell/nitrite solutions are determined after acidification of cooled reaction mixture to pH 4 and extraction and recovery of the product from resulting precipitate using 4:1 (v/v) acetone:water solution. Analysis of variance and Student tests are used to determine differences in mean yield and purity values based on data collected from three replications of each treatment. Significance is determined at a 95% level of probability.

Example 7

Enzyme and Other Means of Reduction

Another aspect of invention related to reduction of antigen applies to agents specifically recognizing the amino acid sequences.

To reduce antigen with the agents specifically recognizing the amino acid sequences, a large number of site-specific agents and their recognition sites are known and commercially available. Examples are as follows (the cleavage sites are indicated with "|" symbol): Hydroxylamine: Asn|Gly, formic acid: Asp|Pro, acetic acid: Asp|Pro, BMPS-skatole: Trp| and o-iodosobenzoic acid: Trp| are the examples of chemical agents. Chymotrypsin: Trp| and Phe|, collagenase: Pro-X|Gly-Pro, endoproteinase Lys-C: Lys|, thrombin: Arg-Gly-Pro-Arg|, and trypsin: Arg| and Lys| are the examples of proteolytic enzymes.

Bovine BSE antigen in the brain and bovine muscle tissue are suspended in 0.1 M ammonium carbonate (concentration; 1 mg/ml), heated for 30 min at 50° C., and then digested with trypsin (TPCK-Tripsin, Sigma Chemical Co., St. Louis, Mo., concentration, 2%) for 1 h at 37° C. Enzymatic reaction is stopped by adjusting pH to 3.0 with 12 N HCl and allowing to stand overnight at 4° C. Optionally undigested antigen and trypsin is removed by ultrafiltration (Centriprep 3, Amicon, Beverly, Mass.). Antigen digested with trypsin is also referred to as "reduced antigen" in the description for a convenience' sake.

The tissue can be further reduced by sodium hypochlorite (bleach) or by a detergent (SDS, phenol, polysorbate 80, Tween 20, Tween 40, Tween 60, Zwittergent 3-12, Teepol HB7 or Span 85) or by protein-crosslinking agent like formaldehyde. Other means of reducing are known such as exposure to ultraviolet light or irradiation by radioactive isotopes. Even exposure to sun or ordinary indoor light for a sufficient period of time will reduce the antigen and tissue into a desired state.

Example 8

Composition Obtained from Tissue or Cell Culture

It is also contemplated that instead of obtaining animal tissues like blood or other tissue as the original source for making the composition one skilled in the art can easily obtain an equally effective composition by conventional tissue and cell culture methods.

In one embodiment, the peripheral blood donated by healthy volunteers is used as a source of human peripheral mononuclear cells (PMNC). PMNC are isolated from blood using Histopaque (Sigma Chemical Co., St. Louis, Mo.) density centrifugation at 1600 rpm for 20 minutes. Isolated PMNC are washed three times with RPMI 1640 medium (J. R. Scientific, Woodland, Calif.) to remove residual Histopaque. After the final wash, PMNC are resuspended in dye-free RPMI 1640 containing 5% fetal bovine serum (Intergen, Purchase, N.Y.). Cultures are incubated at 37 degrees Centigrade in 5% $CO_2$. About 1 to 7 days after inoculation with HIV, the infected cells are harvested and processed including denaturing steps to obtain a composition of the present invention.

Peripheral blood mononuclear cells obtained from HIV-seropositive individuals are equally suitable. These cells can be additionally immortalized by Epstein-Barr virus (EBV) infection. Alternatively instead of PMNC or PBMC, immortalized cell lines can be used for mass production of continuously replicating HIV-infected cells. Such cells can comprise human cell lines H9, MOLT-3, U937, HUT78, CEM, MT-2 among many others and are selected from ATCC collection and propagated accordingly. One of skill in the art can establish equally suitable, alternative cell lines cell line, e.g., kidney cells of an African Green Monkey, by routine art-known methods like inoculating said cell line with a sample containing an inoculum of a virus; incubating said inoculated cell line to permit proliferation of said virus; and harvesting the virus. These and other cells and lines can be easily selected and procured from public and private cell collections (see below).

In a similar manner when cancer vaccine is contemplated, instead of fresh tumor cells obtained from a patient one can select appropriate cancer cell line that derived from a cancer type similar to type of tumor that patient is affected. One can select just one cell line or use pooled non-identical cancer cell lines. For example, to treat a patient suffering from a breast cancer one can use either one or a plurality of pooled MCF-7, CAMA-1, SKBR-3, or BT-20 breast tumor cell lines grown by a conventional method. Literally thousands of such cell lines exist and these cell lines are easily obtained from a large number of tumor cell sources, e.g., American Type Culture Collection or ATCC (www.atcc.org) in Manassas Va.; DCTDC Tumor Repository in Frederick, Md.; The University of Michigan Breast Cell Line/Tissue Bank and Data Base (http://www.cancer.med.umich.edu/umbnkdb.html); ECACC European Collection of Cell Cultures (http://fuseiv.star.co.uk/camr); DSMZ German Collection of Microorganism and Cell Cultures (www.gbf-braunschweig.de/DSMZ); Fujisaki Cell Center or Japanese Cancer Center (http://cellbank.nihs.go.ip) both in Japan, www.biotech.ist.unige.it/interlab/cldb.html in Italy; ECACC European Collection of Cell Cultures in Salisbury, Wiltshire, UK (www-.camr.org.uk/frame.htm); The National Laboratory for the Genetics of Israeli Populations (www.tau.ac.il/medicine/NL-GIP); Coriell Cell Depository (http://locus.umdnj.edu/nia) among many others, the content of which is incorporated herein by way of reference.

Example 9

Composition from Recombinantly Produced Pathogen

With advent of recombinant DNA technology it became possible to employ procaryotic and eucaryotic hosts such as E. coli, yeast, fingi, insect, and mammalian cells in culture to produce useful antigens and fragments thereof. Gene expression is driven by various promoters. Representative promoters suitable for use within the present invention include both eukaryotic (e.g., pol I, II, or III) and prokaryotic promoters, and inducible or non-inducible (i.e., constitutive) promoters, such as, for example, Murine Leukemia virus promoters (e.g., MoMLV), metallothionein promoters, the glucocorticoid promoter, Drosophila actin SC distal promoter, SV 40 promoter, heat shock protein 65 promoter, heat shock protein 70 promoter, immunoglobulin promoters, Mouse polyoma virus promoter ("Py"), rous sarcoma virus ("RSV"), BK virus and JC virus promoters, MMTV promoter, alphavirus junction region, CMV promoter, Adenovirus VA1RNA, rRNA promoter, tRNA methionine promoter, CaMV 35S promoter, nopaline synthetase promoter, and the lac promoter among many others. Based on these one can easily imagine a gene expression unit comprising a DNA coding sequence for a non-bacterial heterologous protein selected from the group consisting of a protein of mammalian origin and a protein of mammalian virus origin, and a regulatory element for transcription of said DNA sequence and translation within a Drosophila cell wherein said regulatory element comprises a Drosophila metallothionein promoter Transformed E. coli cells from a culture expressing high levels (5%) of recombinant HIV antigens are streaked onto an L-Broth plate containing 100 microg/ml ampicillin and the plate is incubated overnight at 37° C. A single colony is inoculated into 10 ml of L-Broth, 100 micro/ml ampicillin and grown overnight at 37° C. An aliquot is used to verify plasmid structure by restriction mapping with SalI and PstI. A second aliquot is used to induce expression of HIV antigens and the rest of the culture is made 15% glycerol by adding ¼ volume of 75% sterile glycerol. Glycerol cell stocks are aliquoted in 1 ml and quickly frozen in liquid nitrogen or dry-ice ethanol bath. These master seed stocks are stored at −70° C. When needed the master seed stock is scraped with a sterile applicator which is used to streak an L-Broth plate containing 100 microg/ml ampicillin. Single colonies from this plate are used to inoculate 20-50 ml of L-Broth/amp, which is incubated at 37° C. overnight. An aliquot of the overnight culture is used to inoculate larger volumes (1-6 liters) of L-Broth/amp. Cells are incubated at 37° C. overnight and reach an OD650 of approximately 5 prior to use as inoculum for the fermenter run. Fermenters (capacity about 16 liters) containing 10l of L-Broth and 1 ml of antifoam are inoculated with 100-500 ml from the inoculum culture. Cells are grown at 37° C. to an OD of about 1. Expression of HIV antigens is induced by addition of 100 ml of an IPTG solution (100 mM) to yield a 1 mM final concentration in the fermenter. Cells are grown for 3 additional hours and subsequently harvested using continuous flow centrifugation. At this step cells can be frozen and kept at −20° C. until further proceedings. Alternatively, 250 liter fermenters are inoculated with 1-5 liter from the inoculum culture. Growth, induction, and harvest are as indicated before. Frozen E. coli cells are thawed and suspended in 2.5 volumes of lysis buffer (0.1M sodium phosphate (NaPi), pH 7.5, 1 mM EDTA, 0.1 M NaCl). Cells are broken in a non-continuous system using a 300 ml glass unit of a Dyno-mill at 3000 rpm and 140 ml of acid-washed glass beads for 15 min. The jacketed chamber is kept cool by a −20° C. ethylene glycol solution. Broken cells are centrifuged at 27,000×g for 25 minutes to remove debris and glass beads. The supernatant is recovered and kept at 4° C. The cell extract is made 30% $(NH4)_2 SO_4$ by slowly adding the ammonium sulfate at 4° C. The extract is stirred for 10 min after the final concentration is achieved, followed by centrifugation at 27,000×g for 20 min. The pellet is resuspended in 1M NaCl, 1 mM EDTA, 1% Triton X-100, and 5% SDS, and then boiled for 5 min. The fraction obtained by selective precipitation is submitted to gel filtration using a G50 Sephadex column equilibrated in 0.03M NaPi, pH 6.8. Chromatography is developed in the same solution. Fractions are collected and absorbance at 280 nm is determined. Antigen-containing fractions are pooled and characterized by protein gel electrophoresis, Western analysis, and ELISA and are further processed into the composition of the invention. It is also equally possible to use these recombinant antigens without these steps of purification.

Alternatively a process for purifying one or more antigenic or immunogenic substances from a source liquid can comprise steps of contacting the source liquid with a chromatography resin; incubating the source liquid with the chromatography resin for a sufficient contact time to allow the resin to bind a desired fraction of one or more antigenic substances, recirculating the chromatography resin in a cross-flow filter; concentrating the chromatography resin and separating contaminants from the chromatography-resin-bound antigens by concentration and/or diafiltration; eluting the antigenic substance from the chromatography resin; and separating the immunogenic substance from the chromatography resin by diafiltration; recovering the desired immunogen(s); and optionally concentrating the antigenic or immunogenic substance.

Example 10

Usefulness of the Composition for Conducting Nonclinical Studies

One of embodiments of the invention is the utility of this composition for nonclinical studies. Those skilled in the art would certainly be interested in studying as to how this composition works. The mechanism of the action of the composition can be studied in variety of ways in vitro and in vivo settings by routine experimentation well known to those of skill in the art. Such nonclinical studies can encompass toxicology, immunology, molecular biology, pharmacology, metabolism, bioanalysis, pharmaceutical analysis, and biosafety testing in support for further development and improvement. One of ordinary skill in the art can easily find relevant experimental protocols and general background information on goals of these experiments by searching appropriate keywords on many sites on Internet, e.g., http://www.lblink.com, http://www.ihuge.com, www.pharmaceuticalonline.com, http://www.mtdesk.com, www.wiley-vch.de/contents/ullmann, www.jimmunol.org, www.freemedicaljournals.com, http://164.195.100.11/netahtml/search-bool.html, http://www.ncbi.nlm.nih.gov/PubMed, the entire content of which is incorporated herein by way of reference. Oral immune tolerance or mucosal immune tolerance in wide sense of the term is a phenomenon, which seldom causes immune responses against an antigen, if it is taken orally. Since any antigen taken orally is absorbed through the intestinal mucosa and then processed by functions of such various tissues as Peyer's patch and epithelial cells of the intestines and the adjacent lymphocytes, portal canal and liver, administration of such antigen rarely causes allergic reaction or shock. The oral immune tolerance has been examined as immunosuppressive therapy for allergy and rejection in organ transplantation. Intranasal administration of the antigen can also induce immune tolerance, which causes no systemic immune response to the antigen, since it is absorbed through the mucosa of the digestive and airway tracts and the lungs.

For example such effects of immune modulation by instant composition can be monitored by assessing cytokine production by lymphocytes isolated from the mice intranasally given the antigen. Cytokines, e.g., IFN-gamma and IL-10 related to inflammation, are determined to examine the effects of stimulation with denatured antigen on production of these cytokines. TGF-beta is known as anti-inflammatory cytokine and immunologically important modulator. DBA/1 mice are given intranasally under anesthesia 0, 0.002, 0.02, 0.2, 2, 20 or 200 microgram of denatured antigen derived from tissues of Rous sarcoma virus infected mice which display visible tumor mass due to virus infection. Alternatively these mice are subcutaneously immunized in their hind paws with a mixture of native antigen (100 microg) and Freund's complete adjuvant (Difco) on day 0. Alternatively, DBA/1 mice are fed on a mixture consisting of lyophilized and then powdered denatured antigen (4%) and commercially available feed during a period of about 1 to 31 days before testing the effect on immune system. After set number of days, lymph nodes are aseptically excised from each mouse. Then, cell suspensions of a single population are prepared and placed ($10^6$ cells/well) in a 96-well microplate (Falcon). After adding serum-free culture medium (X-vivo20, Biowhittaker) and antigen (final concentration 500 microg/ml) to each well, the plates are incubated for 3 days under 5% $CO_2$. After that, the supernatant fluid of the culture medium is collected. The control cells are cultured under similar conditions without antigen or with concanavalin A (final concentration microg/ml) in place of antigen. Since concanavalin A is a mitogen of T cells, it is used to stimulate nonspecifically all the T cells as a positive control. Rat monoclonal antibodies against mouse cytokines (anti-mouse IL-10 monoclonal antibody, JES5-2A5; anti-mouse IFN-gamma monoclonal antibody, RA-6A2; Pharmingen) are coated (50 microl/well) on a microplate (Maxisorp, Nunc). After washing with PBS-Tween, the plate is blocked with 3% BSA-added PBS-Tween. Then, the appropriately diluted culture supernatant described above are added to each well. After washing with PBS-Tween, each of biotin-conjugated rat monoclonal antibodies against mouse cytokines (anti-mouse IL-10 monoclonal antibody, SXC-1; anti-mouse IFN-gamma monoclonal antibody, XMG1.2; Pharmingen) is added to the wells. After another washing with PBS-Tween, avidin-labeled alkaline phosphatase (Zymed) is added. After washing with PBS-Tween, a substrate solution (p-nitrophenyl-2-phosphate) is added to each well and the mixture is allowed to stand for 60 min. The reaction is stopped by adding 5 N NaOH. The concentrations of INF-gamma and IL-10 produced are determined from the absorbance at 405 nm and compared with those of the control samples. Other experimental protocols in studying humoral and cell-mediated immune reactions can be set up to study other aspects of composition and the desirability of a particular protocol will depend on the nature of investigation and particular aim of study of practitioners in the art.

Example 11

Clinical Evaluation of the Composition in HIV-Positive Individuals

Thirty-eight HIV-infected individuals are given the instant composition for several weeks (see results in Table 1). The observed recovery is dramatic and beneficial results are observed in a few days. Patients unable to get up from bed begin walking and some actually return back to work. Remarkable weight gain is observed, particularly with emaciated patients. A higher level of energy and better mood is observed. The placebo effect is unlikely because children are among the patients treated. Children do not comprehend the meaning of the therapy. CD4 counts increase or stabilize and CD8 counts—the markers associated with HIV-killing cytotoxic T lymphocytes (CTL) rise steadily in almost every patient. CTL activity is assessed in freshly isolated peripheral blood mononuclear cells (PBMC) and in phytohaemagglutinin-stimulated interleukin-2 expanded cell lines established from PBMC. Cytotoxicity to HIV-1 env, gag, pol and nef gene products is surveyed in a 4 h 51Cr-release assay using autologous Epstein-Barr virus (EBV) transformed B cells infected with vaccinia constructs expressing each of these HIV genes. The immunodominant CTL epitope and MHC class I antigen restriction specificity of HIV-specific CTL is mapped when present. Plasma viral load is assessed by branched DNA assay or by RT-PCR. Attempts are made to isolate virus from these individuals by the PBMC coculture assay. This and other patient information comprising gender, age, weight, CD4 information, viral load information, HIV genotype and phenotype information, hemoglobin information, neuropathy information, neutrophil information, pancreatitis, hepatic function, renal function, drug allergy and intolerance are collected by routine methods well known in the art.

Patients appear to be able to control their HIV infection by showing vigorous cell-mediated immune response, evident from increase in CD8 cell levels. The composition appears to provide an unexpected benefit to the immune system and to the general well being of the patients.

The dosage varies from patient to patient but commonly 1 to 5 tablets are taken orally every day. No anemia, usually associated with antiviral treatment, is observed with treatment with this composition. The following mild adverse reactions occur in about 50% of patients: mild allergic reaction eg. urticaria, chills, fever, mild abdominal or back pain. No acute, severe allergic reactions (anaphylactic or anaphylactoid) characterised by eg. flushing of the skin, hypotension, substernal pain, bronchospasms, dyspnoea, cardio-respiratory collapse are observed. Such mild reactions can be easily controlled with antihistamines or non-steroid or steroid inflammatory drugs. Usually, after 3-7 days adverse reactions disappear without requiring medical intervention.

Of interest is the observation that prostitutes who take this composition only once or twice do not become infected during 6 months of observation, even though the rate of HIV infection among this population is rather high. Statistically, this cannot be attributed to coincidence.

TABLE 3

Results of treatment of HIV patients with the composition

| No. | Gender | Age | Hospital | Weeks | CD4 | CD8 | WBC | Hemoglo | Hemocrit |
|---|---|---|---|---|---|---|---|---|---|
| Pt 1 | F | 23 | CH | 0 | 429 | 1168 | 7400 | 11.5 | 35.3 |
|  |  |  | CH | 19 | 670 | 2820 | 11200 | 12.3 | 36 |
| Pt 2 | M | 27 | CHU | 0 | 12 | 392 | 5600 |  |  |
|  |  |  | CH | 19 | 20 | 520 | 7200 |  |  |
| Pt 3 | F | 25 | CHU | 0 | 347 | 942 | 5900 | 13.1 | 40.1 |
|  |  |  | CH | 24 | 380 | 970 | 5300 | 13.7 | 40 |
|  |  |  | ATRCS | 54 |  |  |  |  |  |
| Pt4 | M | 28 | CHU | 0 | 32 | 294 | 3100 |  |  |
|  |  |  | CH | 7 | 10 | 460 | 4200 |  |  |
| Pt 5 | F | 28 | CHU | 0 | 436 | 742 | 5240 |  |  |
|  |  |  | CHU | 27 | 647 | 1079 |  |  |  |
| Pt 6 | M | 35 | CH | 0 | 0 | 300 | 5700 |  |  |
|  |  |  | CH | 8 | 0 | 690 | 4900 |  |  |
| Pt 7 | M | 48 | S | 0 | 140 | 1390 |  |  |  |
|  |  |  | CHU | 8 | 174 | 1792 | 6600 |  |  |
| Pt 8 | M | 36 | S | 0 | 108 | 1079 | 5700 |  |  |
|  |  |  | CHU | 29 | 241 | 1757 | 5900 |  |  |
| Pt 9 | F | 35 | S | 0 | 440 | 520 |  |  |  |
|  |  |  | CHU | 18 | 551 | 735 | 4500 |  |  |
| Pt 10 | M | 33 | S | 0 | 17 | 645 | 3300 |  |  |
|  |  |  | CHU | 29 | 57 | 614 | 4700 |  |  |
| Pt 11 | F | 32 | S | 0 | 76 | 531 | 3700 |  |  |
|  |  |  | CHU | 29 | 101 | 495 | 4200 |  |  |
| Pt 12 | M | 31 | CH | 0 | 530 | 1580 | 7800 | 15.1 | 43 |
|  |  |  | CH | 6 | 465 | 2030 | 8100 | 15.1 | 44 |
| Pt 13 | F | 25 | CH | 0 | 230 | 530 | 5500 |  |  |
|  |  |  | CH | 5 | 320 | 690 | 6300 |  |  |
| Pt 14 | F | 36 | CH | 0 | 230 | 530 | 4500 |  |  |
|  |  |  | CH | 9 | 210 | 1340 | 4300 |  |  |
| Pt 15 | F | 41 | R | 0 | 270 | 900 | 5100 |  |  |
|  |  |  | R | 3 | 310 | 1070 | 6600 |  |  |
| Pt 16 | F | 33 | R | 0 | 440 | 1680 | 6000 |  |  |
|  |  |  | R | 2 | 630 | 1720 | 5800 |  |  |
| Pt 17 | M | 35 | R | 0 | 10 | 490 | 4600 |  |  |
|  |  |  | R | 2 | 10 | 520 | 3600 |  |  |
| Pt 18 | F | 26 | BPL | 0 | 438 |  | 8500 |  |  |
|  |  |  | V | 34 | 360 | 1110 | 5200 |  |  |
|  |  |  | ATRCS | 45 |  |  |  |  |  |
| Pt 19 | M |  | BA | 0 | 141 |  |  |  |  |
|  |  |  | BA | 58 | 272 |  |  |  |  |
| Pt 20 | M | 30 | BPL | 0 | 605 |  |  |  |  |
|  |  |  | BPL | 30 | 970 | 856 |  |  |  |
|  |  |  | AI | 32 |  |  | 9900 |  | 45 |
| Pt 21 | F | 50 | CH | 0 | 400 | 1920 | 7600 |  |  |
|  |  |  | CH | 32 | 520 | 2330 | 8400 |  |  |
| Pt 22 | M | 26 | CH | 0 | 0 | 240 | 3900 |  |  |
|  |  |  | CH | 9 | 0 | 350 |  |  |  |
| Pt 23 | F | 31 | CHU | 0 | 240 | 888 | 6900 | 11.7 | 34.7 |
|  |  |  | CHU | 30 | 200 | 1077 | 7800 | 12 | 35.2 |
| Pt 24 | M | 28 | CH | 0 | 0 | 180 | 5900 |  |  |
|  |  |  | CH | 38 | 0 | 100 | 22300 |  |  |
| Pt 25 | F |  | CHU | 0 | 218 | 629 | 9170 | 13.1 | 40.5 |
|  |  |  | CHU | 31 |  |  |  |  |  |
| Pt 26 | F | 60 | RA | 0 | 175 | 437 |  |  |  |
|  |  |  | RA | 65 | 237 | 1163 | 5120 |  |  |
| Pt 27 | M | 20 | SR | 0 | 195 |  | 5100 |  |  |
|  |  |  | V | 26 | 100 |  | 9600 |  |  |
| Pt 28 | F | 35 | CH | 0 | 350 | 1560 | 9400 |  |  |
|  |  |  | CH | 28 | 280 | 1890 | 8000 |  |  |
|  |  |  | ATRCS | 44 |  |  |  |  |  |
| Pt 29 | M | 37 | YBON | 0 | 30 | 1110 |  |  |  |
| Pt 30 | M |  |  |  |  |  |  |  |  |
| Pt 31 | M | 34 | CH | 0 | 139 | 1034 |  |  |  |
| Pt 32 | F | 30 | CH | 0 | 559 | 1737 |  |  |  |
| Pt 33 | M | 4 | CH |  |  |  |  |  |  |
| Pt 34 | M | 27 | V | 0 | 160 |  | 7400 |  |  |
|  |  |  | V | 32 | 50 |  | 9100 |  |  |
| Pt 35 | F | 39 |  |  |  |  |  |  |  |
| Pt 36 | M | 32 | CHU | 0 | 195 | 1098 | 5400 | 14.9 | 45.9 |
|  |  |  | CHU | 24 | 140 | 1242 | 6000 | 14.8 | 44.5 |
| Pt 37 | F | 34 | CH | 0 | 13 | 797 | 4600 | 6.9 | 23 |
|  |  |  | ATRCS | 8 |  |  |  |  |  |

TABLE 3-continued

Results of treatment of HIV patients with the composition

| No. | Gender | Age | Hospital | Weeks | CD4 | CD8 | WBC | Hemoglo | Hemocrit |
|---|---|---|---|---|---|---|---|---|---|
| Pt 38 | F | 56 | CH | 0 | 400 | 1920 | 7600 | 13.8 | 41 |
|  |  |  | CH | 23 | 540 | 2630 | 8800 | 14 | 42 |

HOSPITAL OR WHERE TEST IS CONDUCTED
AI = Aikchol
ATRSC = Anonymous Treatment Red Cross Society
B = Bangkok General Hospital
BA = Bangkok Lab
BPL = Bangkok Pathology Laboratory
CH = Chonburi Hospital Example 12

Shrimp Composition

Shrimp composition can be made by any of specific processes disclosed supra or by using the protocol as follows. A species of living shrimp are placed in fresh water or an aqueous salt solution containing not greater than 0.3% by weight, preferably not greater than 0.1% by weight, of at least one compound selected from organic acids such as acetic acid, citric acid, succinic acid, malic acid, tartaric acid and lactic acid; inorganic acids such as phosphoric acid, sulfuric acid and hydrochloric acid; and sodium or potassium salts of these acids. The aforesaid solution can also be characterized as a slightly acidic aqueous solution having a pH of 3 to 6.5. These living shrimp are left therein at a temperature of 1° to 25° C., preferably 2° to 15° C., for a period of 0.5 to 72 hours, preferably 1 to 40 hours. Thus, the alimentary canal of the living shrimp is substantially freed of soil by their own excretory power. Then, the living shrimp are washed with water to remove any dirt from the body surfaces thereof. These washing steps are however optional. Thereafter, the living shrimp are wet-ground and the resulting suspension is frozen at a low temperature of −5° C. or below, preferably −10° to −60° C. Then, the frozen suspension is freeze-dried and vacuum-dried. Specifically, while the temperature is raised stepwise from −60° to +90° C., preferably from −40° to +80° C., the suspension is freeze-dried and then vacuum-dried under a vacuum of 100 mmHg or below, preferably 30 mmHg or below, for a period of 5 to 100 hours, preferably 10 to 60 hours. Thus, there is obtained sterile dried shrimp powder. To insure the denaturation the powder is then autoclaved for about 20 minutes at 121° C.

In the step of wet-grinding the shrimp, i.e., the step of destroying the tissues (or cells) of the shrimp, it is preferable to form the shrimp into a suspension or homogenate by means of a suitable device such as homogenizer, blender, homo-mixer, smasher or pressurized cell destroyer. This wet-grinding step is desirably carried out at a temperature of 1° to 25° C. and preferably 2° to 15° C. Alternatively, shrimp is dried first by freeze-drying and then ground into fine powder.

According to either of the above-described processes, dried shrimp powder having a yellowish or brown color can be obtained from shrimp. In ordinary cases, the dried shrimp powder is prepared so as to, have a moisture content of 5 to 16%, preferably 7 to 14%, an ash content of 3 to 8%, preferably 4 to 7%, and a nitrogen content of 1 to 11%, preferably 6 to 11%. The dried shrimp powder thus obtained contains baculovirus antigens and shrimp tissues.

The composition is equally suitable for preventing the mortality due to disease in commercially farmed fish like salmon or trout, e.g., Fish Pancreas Disease Virus (FPDV). This industry involves not thousands of dollars, but hundreds of millions of dollars. The present invention provides a method for the protection, service to and salvage of a multibillion dollar industry; and also aids in providing a vaccine to a world where maintenance of the food supply is becoming an ever increasing problem.

Example 13

Use of the Composition as a Preventive Vaccine

Shrimp is a crustacean which belongs to the Genus Penaeus. Wild shrimp has been caught for food for centuries. Many species of shrimp can be nowadays cultivated, e.g., highly praised Tiger Prawn (Penaeus monodon, Fabricius). Shrimp farming is a worldwide industry with a large market and approximately half of the shrimp consumed in the United States is from farms. While shrimp farming is a lucrative business, there are serious drawbacks associated with farming the dense populations of shrimp in close quarters, of particular concern is the susceptibility of these animals to viral and bacterial infections.

One of many viral infections is caused by Monodon baculovirus (MBV) which belongs to Baculoviridae family of viruses which preferentially replicate in insect tissues. The infected prawn display yellow cream colored hepatopancreas and expand in size. The exterior appearance is also yellow in color and thus the Baculovirus-caused disease is sometimes referred to as Yellow Head Disease. Other pathogenic Baculoviruses are also known such as Baculovirus penaei (BP), Baculovirus mid gut gland necrosis (BMN). These viruses infect diverse species of prawn such as P. japonicus, P. duorarum, P. stylirostris, P. vannamei, P. aztecus, and P. marginatus among many others. Moreover the Hepatopancreatic parvo-like virus (HPV) infects P. merquiensis species in Australia, P. orientalis in Singapore, P. chinensis in China and P. monodon. in Philippines. In addition to viruses pathogenic microbial infections in shrimp are also common, especially those caused by family of Vibrio and Aeromonas, e.g., vibrio diseases of Kuruma prawn (Penaeus japonicus), Giant tiger prawn (Penaeus monodon), White-leg shrimp, Vibrio anguillarum, or the like; parasitic diseases of Epistylis sp., Soothamnium sp., Ichthyopthiriasis or the like; mycotic infectious diseases of Lagenidium sp., Siropidium sp., or the like. The present composition prepared according to the art-known process selected from one of disclosed examples and comprises denatured (non-live) Baculovirus-infected shrimp tissues and Baculovirus antigens.

The obtained composition appears as a freely flowing powder and individual particles exhibit a crystalline appearance. This preparation is then spiked into a standard shrimp meal at a desired concentration. Typical shrimp meal consists of Fish head meal, Squid meal, Soybean meal, Cereal products or by-products, Fish oil, Soybean lecithin, Cholesterol, Binder, Dicalcium phosphate, Vitamins, and Trace minerals mix. Usually, the effective dose of composition ranges from about 0.01 to 500 gram per kg of shrimp meal, preferably from about 0.1 to 20 gram, more preferably from about 6 to 16 gram, but the final and optimal dose may vary depending on desired result and aquaculture conditions.

Shrimp meal prepared by this process is fed either to non-infected shrimp population in the aquaculture or to already infected sick shrimp. The composition is equally effective in both circumstances.

Use of composition as a preventive or prophylactic preparation or vaccine is made. Freshly seeded shrimp larvae that have not been fed with the composition contract the virus present in the water and die as a result by the end of 8 weeks. By contrast there is a clear dose-dependent survival rate among shrimp fed with increasing concentration of the composition.

About 1 kg of shrimp meal is adequate per about 100,000 shrimp aged from about 1 to 15 days and meal particle size for this age is about 100 micron. Correspondingly, it is preferable that about 1.3 kg will be sufficient per 100,000 shrimp aged 20 days and meal particle size at this stage can be slightly bigger at about 200 micron. Similar adjustments can be made depending on age and population size of shrimp, e.g., about 1.8 kg/100,000 age 25 days at meal size about 200 micron; 2.5 kg/100,000 age 30 days at meal size 200 micron; 3.5 kg/100,000 age 40 days at meal size 300 micron; 4.0 kg/100,000 age 50 days at meal size 300 micron; 5.0 kg/100,000 age 60 days at meal size 400 micron, and alike. The composition is administered about 8 times during the period of vaccination, although the frequency of feeding and meal quantity can vary depending on desired result.

Thus while various alterations in the protocol can be made and established by routine experimentation familiar to those of skill in the art, this example illustrates clearly the broad applicability of the inventive concept across a wide variety of animal species.

Example 14

Microbial Infection of Unknown Etiology

Every year new pathogenic microbes and viruses are added to the growing list of infectious diseases. Since 1973 many new species have been added, e.g., 1973 Rotavirus Virus Major cause of infantile diarrhea; 1975 Parvovirus B19 Virus Aplastic crisis in chronic hemolytic anemia; 1976 *Cryptosporidium parvum* Parasite Acute and chronic diarrhea; 1977 Ebola Virus Ebola hemorrhagic fever; 1977 *Legionella pneumophila* Bacteria Legionnaires' disease; 1977 Hantaanvirus Virus Hemorragic fever with renal syndrome (HRFS); 1977 *Campylobacter jejuni* Bacteria Enteric pathogens distributed globally; 1980 Human T-lymphotropic Virus T-cell lymphoma-leukemia virus I (HTLV-1); 1981 Toxic producing strains of *Staphylococcus aureus* Bacteria Toxic shock syndrome (tampon use); 1982 *Escherichia coli* 0157:H7 Bacteria Hemorrhagic colitis; hemolytic uremic syndrome; 1982 HTLV-II Virus Hairy cell leukemia; 1982 *Borrelia burgdorferi* Bacteria Lyme disease; 1983 Human immunodeficiency virus (HIV) Virus Acquired immunodeficiency syndrome (AIDS); 1983 *Helicobacter pylori* Bacteria Peptic ulcer disease; 1985 *Enterocytozoon bieneusi* Parasite Persistent diarrhea; 1986 Cyclospora cayatanensis Parasite Persistent diarrhea; 1988 Human herpesvirus-6 (HHV-6) Virus Roseola subitum; 1988 Hepatitis E Virus Enterically transmitted non-A, non-B hepatitis; 1989 Ehrlichia chafeensis Bacteria; Human ehrlichiosis; 1989 Hepatitis C Virus Parenterally transmitted non-A, non-B, liver infection; 1991 Guanarito virus Virus Venezuelan hemorrhagic fever; 1991 Encephalitozzon hellem Parasite Conjunctivitis, disseminated disease; 1991 New species of *Babesia* Parasite Atypical babesiosis; 1992 *Vibrio cholerae* 0139 Bacteria New strain associated with epidemic cholera; 1992 *Bartonella henselae* Bacteria Cat-saatch disease; bacillaryangiomatosis; 1993 Sin nombre virus Virus Adult respiratory distress syndrome; 1993 *Encephalitozoon cuniculi* Parasite Disseminated disease; 1994 Sabia virus Virus Brazilian hemolrhagic fever; and 1995 HHV-8 Virus Associated with Kaposi sarcoma in AIDS patients among many others.

The present invention is particularly useful in treating and preventing viral and bacterial infections in which the causative pathogen has not been identified and thus no therapy is available. This composition is equally suitable for treating pathogens of known origin but for which no therapy has yet been developed.

For instance, a colony of captivated rhesus monkeys in a zoo begin dying from a rapidly evolving disease. The symptoms of jaundice and haemorrhagic manifestations are observed (epistaxis, haematemesis, melaena and uterine bleeding) followed by albuminuria, coma and death two to three days later. An infection with unknown virus is suspected and normally the only available remedy in this situation is the quarantine and destruction of the entire colony. However, one monkey is bled and a composition is prepared from the blood of the infected animal. This composition is then fed to five sick monkeys who rapidly recover. The composition is administered to all sick as well as non-infected monkeys.

A larger batch is made from pooled blood of several infected primates and this preparation is administered orally to the entire colony.

Example 15

Influenza Vaccine Preparation

Fertilized chicken eggs are inoculated with a strain of Influenza prevalent during current season, e.g., virus Type B or subtypes H1N1 and H3N2 of Influenza Type A. The inoculation is carried out by art-established procedures, i.e., by injection of a small volume of virus into the allantoic cavity. In the prior art very extensive purification steps are required to separate the virus from egg protein. According to the principles of this invention this step is not anymore required. The whole mass of egg liquid is obtained by breaking the shells of eggs and is simply spray-dried at a blowing temperature of 175° C. This reduction step results in dry egg powder comprised substantially of spherical particles having an average particle diameter of 100 micrometer. The powder is then optionally autoclaved or in the absence of an autoclave the dry egg powder is spread on a cloth laid over a steamer and exposed to steam at 100° C. for 2 minutes to conduct heat denaturation, thereby to produce the processed egg powder of the present invention. At the upper part of the steamer is provided a cover preventing dropping of condensed water on the egg powder. Alternatively the processed egg powder is added quickly to an equivalent weight of boiling with stirring in a mixer, and the mixture is left standing for about 3-10 minutes. These products are then prepared as conventional egg powder product and given to as a breakfast supplement to vaccinate humans against seasonal influenza outbreak.

This composition can be equally applied for veterinary purposes, e.g., for treating or preventing RNA-containing equine influenza viruses, which belong to the family Orthomyxoviridae. Equine influenza virus, and other unrelated pathogens like equine protozoan myeloencephalitis or whooping cough.

Example 16

Malaria Vaccine

Malaria is one of the world's biggest killers—more than 2 million people die from it every year, and hundreds of millions are infected. While most infectious diseases are caused by bacteria or by viruses, malaria is caused by a *Plasmodium* endoparasite, which enters into host's body with mosquito bites. Despite intensive research a vaccine is yet to be produced. Several vaccines have been developed based on the Circumsporozoite (CS) protein but all of them failed since they are focused on one or few antigens.

If malaria infected mosquito is prepared as a composition according to principles of the invention and given to naïve subjects they can develop immunity against malaria.

The present composition prepared according to instant principles comprises over 2000 proteins and even higher number of antigens synthesized by asexual stage malaria in mosquito gut tissues. Subjects taking the instant preparation orally fail to become infected with malaria. Infected patients who are given the ground mosquito pills show signs of recovery from the disease. Hence, the present composition is effective as a therapeutic and a preventive remedy not only against viruses and bacteria but also against malarial parasites, especially those spread by *Anopheles* sp., i.e., *Plasmodium falciparum, P. malariae, P. vivax,* and *P. ovale*.

In considering these results it is apparent that other arthropod-borne pathogenic diseases either viral, bacterial, or protozoan or other parasites can be treated. These include but are not limited to those spread by Mite: *Leptotrombidium* sp. (red mites) Scrub Typhus (Tsutsugamushi disease) *Rickettsia tsutsugamushi* (bacteria, intracellular); Mite: *Liponyssiodes sanguineus* (mouse mite) Rickettsial pox *Rickettsia akari* (bacteria); Tick: *Dermacentor* sp. Tularemia *Francisella tularensis* (Gram negative bacteria); Tick: *Dermacentor* sp. and other Ixodid ticks Rocky Mountain Spotted Fever *Rickettsia rickettsia* (bacteria); Tick: *Ornithodoros* sp. Endemic Relapsing Fever *Borrelia* sp. (bacteria, spiral shaped); Tick: *Ixodes* sp. Babesiosis *Babesia microti* (parasite, protozoan); Tick: *Ixodes* sp. Lyme disease *Borrelia burgdorferi* (bacteria, spiral shape); Tick: *Dermacentor variabilis, Amyblyomma americanum* Ehrlichiosis, Sennetsu fever *Ehrlichia canis E. sennetsu E. chaffeensis E. equi E. phagocytophilia* (bacteria, intracellular); Tick: *Dermacentor* sp. Colorado Tick Fever CTF virus, Eyach virus, or strain S6-14-03 (Reoviridae); Tick: Russian Spring-Summer Encephalitis, Louping Ill Encephalitis, Langat Encephalitis, Powassan Encephalitis, Omsk hemorrhagic fever Russian Spring-Summer Encephalitis, Louping Ill Encephalitis, Langat virus, Powassan virus, Omsk hemorrhagic fever virus (Flaviviridae); Tick: Nairobi Sheep fever, Crimean hemorrhagic fever Nairobi sheep disease virus, Crimean-Congo hemorrhagic fever virus (Bunyaviridae); Crustacea Copepod: *Cyclops* sp. Diphyllobothriasis, fish tapeworm *Diphyllobothrium latum* (parasite, cestode, tapeworm); Strongyles, Ascarids, hookworms, lungworms, filarial worms, whipworms; Copepod: *Cyclops* sp. Sparganosis *Diphyllobothrium spirometra* (parasite, cestode, tapeworm); Copepod: *Cyclops* sp. Dracunculosis *Dracunculus medinensis*; Crabs, crayfish: various freshwater species Paragonimiasis *Paragonimus westermani*; Lice: *Pediculus humanus* Epidemic typhus *Rickettsia prowazekii* (bacteria); Lice: *Pediculus humanus* Trench fever, bacillary angiomatosis, bacillary peliosis *Bartonella quintana* (Gram negative bacteria); Lice: *Pediculus humanus* Louse-borne relapsing fever or epidemic relapsing fever *Borrelia recurrentis* (bacteria; spiral shape); Flea: *Xenopsylla cheopis*, and various other rodent fleas Plague *Yersina pestis* (Gram negative rod shaped bacteria); Flea: *Xenopsylla cheopis* Murine typhus *Rickettsia typhi* (bacteria); Flea: *Xenopsylla cheopis*, and various other rodent fleas Rat tapeworm infection *Hymenolepsis diminuta* (parasite; cestode; tapeworm); Flea: various species Dog tapeworm infection, Dipylidiasis *Diphylidium caninum* (parasite; cestode; tapeworm); Bug: *Triatoma* species, *Panstrongylus* sps (Kissing assassin bug, Reduvid bug) Chaga's disease *Trypanosoma cruzi* (parasite; protozoan); Beetles: flour beetle *Hymenolepsis Hymenolepsis nana* (parasite; tapeworm; cestode); Fly, gnat: *Glossina* sp. (tsetse fly) African trypanosomiasis, African sleeping sickness *Trypanosoma brucei rhodesiense* and *T.b. gambiense*; Fly, gnat: *Simulium* sp. (black fly) Onchocerciasis, River blindness *Onchocerca volvulus* (parasite; round worm; nematode); Fly, gnat: *Chrysops* sp. Tularemia *Francisella tularensis* (Gram negative rod shaped bacteria); Fly, gnat: *Phlebotomus* sp., *Lutzomyia* sp. (sandflies) Leishmaniasis *Leishmania donovani* (Visceral, durndum fever, kala-azar), *L. tropica* (cutaneous; oriental sore, Delphi boil), *L. braziliensis* (mucocutaneous; espundia, american leishmaniasis, chiclero ulcer) (parasite; protozoan); Fly, gnat: *Phlebotomus* sp. (sandfly in Peru, Ecuador and Columbia) Bartonellosis, Oroya fever, Carrion's disease *Bartonella bacilliformis* (Gram negative bacteria); Fly, gnat: *Chrysops* sp. (mango flies) Loaiasis, Eye worm *Loa loa* (parasite; nematode; roundworm); Fly, gnat: sandfly Sandfly fever, Rift Valley fever Sandfly fever Naples virus, Sandfly fever Sicilian virus, Rift valley fever virus (Bunyaviridae); Mosquito: various species Bancroftian filariasis, filarial Elephantiasis *Wuchereria bancrofti* (parasite; nematode; roundworm); Mosquito: various species Malayan filariasis, filarial Elephantiasis *Brugia malayi* (parasite; nematode; roundworm); Mosquito: various species Dirofilariasis *Dirofilaria immitis* (parasite; nematode; roundworm); Mosquito: *Aedes aegypti* Yellow fever Yellow fever virus (Flaviviridae); Mosquito: *Aedes* sp. Dengue fever, Break Bone fever Dengue fever virus (Flaviviridae); Mosquito: *Culiseta melanura, Coquillettidia pertubans, Aedes vexans* Eastern Equine encephalitis Eastern Equine Encephalitis virus (Togaviridae); Mosquito: *Aedes triseriatus* La Crosse encephalitis La Crosse Encephalitis virus (Bunyaviridae); Mosquito: *Culex* sp. St. Louis encephalitis St. Louis Encephalitis virus (Flaviviridae); Mosquito: *Culex* sp., *Culex tarsalis* Venezualan equine encephalitis, Western equine encephalitis Venezualan Equine Encephalitis virus, Western Equine Enchephalitis virus (Togaviridae); Mosquito Chikungunya forest fever Chikungunya virus, Mayaro fever, Mucambo fever, O'Nyong-Nyong fever, Pixuna fever, Ross River fever (Togaviridae) Mosquito fevers and encephalitis Nile fever, Japanese encephalitis virus, West Nile fever, Zika fever, Wesselsbron fever, Kyasanur forest disease virus (Flaviviridae); Mosquito fevers and encephalitis Oropouche virus, Bunyamwera, Bwamba fever, Guama fever, Oropouche fever, California Enchephalitis virus (Bunyaviridae); Mosquito fevers Chandipura fever, Piry fever (Rhabdoviridae) among many others.

Example 17

Fibromyalgia

The subject a 27 years old female is presented with fibromyalgia. Symptoms included chronic fatigue, stomach disorders, pain and swelling in all joints, amenorrhea and swelling in the breasts. The patient is diagnosed approximately five years before beginning treatment. Patient had been taking on a daily basis 650 mg of tylenol and formulation of tylenol with codeine. The subject's 24-hour base pre-therapy prolactin levels are high throughout the day. For the first 4 weeks of treatment, the patient is administered 625 mg of composition which is prepared from small sample of joint biopsy according to the process of the invention. Prolactin profiles are measured and show that the patient's daytime prolactin levels is reduced. The clinical improvements in this patient also includes discontinuation of both tylenol and codeine, and reduction in the following symptoms: fatigue, stomach disorders and pain in all joints. In addition, a normal menstrual cycle is restored and swelling of breasts significantly subsided.

Example 18

Crohn's Disease 20 years old male is presented who is diagnosed with Crohn's disease based on exploratory surgery and barium X-ray. Approximately 12 inches of the small intestine show inflammation. The subject initially received prednisone 40 mg/day which did not made any improvement to his condition. A composition is then prepared using tissue obtained from surgery. After two months of daily intake of one pill prepared of intestinal tissue the clinical improvements to this patient include following: (1) avoidance for surgical resection within this time period; (2) no increase in inflamed area of intestine despite discontinuance of prednisone, based on a comparison of X-rays from first diagnosis with most recent; (3) during the time from first diagnosis to end of treatment scarring is minimal as determined by intestinal response to prednisone treatment; and (4) the patient reports no major intestinal discomfort during treatment despite no major dietary changes from pre-diagnosis.

Example 19

Prevention of Kidney Transplant Rejection

In this experiment a right nephrectomy is performed on 10 mice at the same time an allograft (kidney transplant from a different strain of mouse) is performed. All ten of the animals are observed for the first five days without immunosuppressive therapy. Non-treated control animals receiving a nephrectomy and an allograft kidney transplantation, exhibit initial signs of severe rejection around day 5 post-transplantation. Five of the animals (treated group) are given daily along with standard food pellets a small dose of formulated (denatured and crystallized powder of murine kidneys admixed and made into food pellets) composition for the next five days. Animals are fed ad libitum but the consumed dose does not usually exceed 10 mg of pure kidney composition per day. All five treated animals experience rapid reversal of their rejection symptoms, including a return to normal levels of creatinine and eventually live beyond 100 days. The untreated control animals are all dead by day ten due to acute organ rejection. These results with respect to avility to overcome the immune rejection are significant in confirming that the present composition is highly effective in suppressing an inflammatory immune response.

Example 20

Anti-STD and Contraceptive Product

The present invention can be useful against pathogens for sexually transmitted diseases (STDs) of viral and bacterial origin as well as a new prophylactic contraceptive method. For women, intrauterine devices (IUDs) and intravaginal devices (IVDs) can be designed that release antigens into the uterus or into the vagina to provide continuous priming/protection against pregnancy and STDs for periods of months to years. For example for men a skin lotion can be formulated containing sperm and STD antigens to be applied to the penis and external genitals during sexual activity, thereby delivering prophylactically effective doses of antigen to virtually all areas of skin and epithelia across which most STDs, including AIDS, are usually transmitted, and, during vaginal or rectal intercourse, the penis will deliver a contraceptively reliable dose of the sperm immunogen to the cervical region of the vagina.

Example 21

Kaposi Sarcoma (KS) Treatment

Kaposi's sarcoma, the most common malignancy in AIDS patients. HIV-seropositive patients with confirmed KS that progressed over several months before enrollment are given an initial dose of 850 mg/day of oral composition of the invention in an open label study for 2 months. Toxicity, tumor response, immunologic and angiogenic factors, and virologic parameters are assessed on a regular basis. Twenty patients aged 21 to 47 years with a median CD4 count of 240 cells/$mm^3$ are enrolled. All patients are assessable for toxicity and response. Minor stomach and intestinal disturbances (diarrhea) in seven patients and mild and transient headache in three patients are the most frequent notable symptoms of toxicity. Positive side-effects include improved mood, libido, and lean body mass weight gain. Eight (47%; 95% confidence interval [CI], 23% to 72%) of the 17 assessable patients show a complete response, and additional two patients a partial response consisting of no-progression in size or number of lesions and drying of moist lesions. Based on all 20 patients treated, the response rate is over 50% (95% CI, 19% to 64%). The median composition dose at the time of response is 850 mg/day. The median duration of drug treatment is 6 months. Thus, oral composition of the invention is well tolerated in this population of patients for as long as 24 months and is found to induce clinically meaningful anti-KS responses in a sizable subset of the patients. It is of particular importance that instant composition useful in treating KS is the same composition useful in treating AIDS patients in Example 11.

Thus composition and method for cancer therapy useful in treating human patients with tumors to inhibit recurrence and formation of metastases. This will for example comprise surgically removing tumor tissue from a human cancer patient, reducing the tumor tissue to small fragments, e.g., powder, denaturing the fragments, formulating into a pill, and administering the vaccine orally into the human patient for a period of time sufficient, e.g., 5 years, to assure that metastases or cancer does not recur.

Example 22

Tuberculosis Treatment

*Mycobacterium tuberculosis* or *Tuberculum bacilli* (T. B.) grows in the endobronchial space and is found in the sputum of infected individuals. During exacerbations of infection, such growth also occurs in the alveoli. Tuberculosis is a highly infectious disease that is characterized by the inflammation and progressive destruction of lung tissue. The debilitation of the lungs in patients with tuberculosis is associated with accumulation of purulent sputum produced as a result of chronic endobronchial infections caused by *Mycobacterium tuberculosis*. Nearly all individuals suffering from tuberculosis eventually die of respiratory failure. Presently, administration of drugs, such as aminoglycosides kanamycin, streptomycin and amicacin as well as isoniazid is the treatment of choice for tuberculosis patients. However, penetration of these drugs into the bronchial secretions is poor and treatment is often ineffective especially against drug resistant bacteria.

Sputum from tuberculosis patients is collected and prepared into anti-tuberculosis therapeutic vaccine in a manner similar to vaccine preparation from a blood. Aerosolized substance is then administered with aid of jet nebulizers, e.g., Sidestream (Pari Respiratory Equipment, Richmond, Va.). Patients receive serial doses of 300 mg of the composition (5 mL of a 60 mg/mL solution) from jet nebulizers. Twenty patients are enrolled in each study. Each patient receives, in random order, placebo or active administration from nebulizer delivery system. The doses are separated by at least 2 days and not more than 5 days. Airway irritation and acute bronchospasm are assessed by measuring spirometry immediately prior to and 30 min post-completion of aerosol administration. A decrease in forced expiratory volume >15% in the 30 min spirometry test is considered evidence of bronchospasm. All patients with underlying disease of tuberculosis, confirmed at entry by the inclusion/exclusion criteria specified in this protocol, are eligible for enrollment into the study. Investigators at the participating TBC centers select patients that meet all of the inclusion criteria and one of the exclusion criteria. Eligible patients are admitted to the study center on the day of the study and receive aerosol therapy if they fulfill entrance criteria. Physical exam is administered by a physician or RC nurse prior to initial aerosol treatment only. Vital signs, height, weight, oximetry, assessment of current respiratory status and brief medical history are recorded. Patients sat upright and used nose clips during the aerosol administration. The total duration of time and the number of inhalations required to complete the aerosol treatment are recorded. Any evidence of wheezing or respiratory distress are recorded as well as number of rest periods required by the subject because of dyspnea or excessive coughing during the administration period. Following the last aerosol treatment of the study, patients receive a physical exam to evaluate clinical improvement.

One does not need to follow exactly the procedure described above and can instead of collecting a sputum or bronchial lavage order a necessary microorganism from a depository. Numerous depositories exist wherein one can easily select desired pathogen, e.g., The Belgian Coordinated Collections of Microorganisms (BCCM) at www.belspo.be/bccm; The Culture Collection of Algae and Protozoa at www.ife.ac.uk/ccap; Dutch Centraalbureau voor schimmelcultures at www.cbs.knaw.nl; Microbial Information Network of China at www.im.ac.cn among many others, the content of which is incorporated herein by way of reference.

Example 23

Pyoderma Treatment

Patients with pyoderma, including furunculitis, cellulitis, and folliculitis, are treated with the composition along with a control group which is not treated. Medications are administered either orally or intranasally for 5 consecutive days. Immunological indices are normalized with disappearance of skin manifestations and relapses are prevented after treatment with instant. Clinical improvement correlate with immunological indices correction. Administration intranasally or topically as a sterile saline solution of medication for a period of 5 to 10 days at a concentration of 1 mg/kg body weight. A number of patients within the group patients afflicted with furunculitis, pyoderma, cellulitis, and folliculitis are afflicted with acne vulgaris and acne. The immunological indices are corrected and normalized rapidly within the group therapy. The clinical outcome correlates with the correction of immunological indices, and relapses are controlled.

Example 24

Pelvic Inflammation

Female patients with the various disorders (pelvic inflammatory diseases, cervicitis, vaginitis and various tubo-ovarian and adnexal abscesses) are treated and some patients are used as controls. The composition is given intravaginally at 100 mg for 5 consecutive days or 50 mg intranasally for 5 consecutive days in conjunction with conventional therapy. The clinical effect of is expressed as the arresting of pain syndrome, the control of body temperature, e.g. reduction of fever, the decrease of duration of conventional treatment. The normalization of immune status correlates with clinical improvements.

Example 25

Herpes Outbreak

Patients treated with the composition topically or intranasally. They experience marked reduction of recurrence of herpetic lesions, with substantial reduction in the period between outbreaks. Treatment in combination with interferon also shows a lessening of lesion outbreaks.

In a separate trial patients with Herpes Zoster are treated with the composition in combination with conventional interferon treatment and some control patients with interferon alone. Administration single daily oral or intranasal 100 mg dose during a period of 10 days results in accelerated regression of foci of herpetic infection. The healing occurs earlier than in control groups.

Example 26

Gingival Disease

Patients are treated for gingival disease by buccal administration of the composition in the area of the gingiva. The treatment results in the arresting of gingival disease. Administration of 100 mg bucally or by electrophoresis (whereby a small voltage charge to the gums results in a rapid transfer of medication through the gum epithelium) results in the arresting of bleeding, more rapid restoration of inflammatory processes, and the decrease of purulent discharge. The treatment results in fewer recurrences of the disease and appearance of normal gums for longer time period than in controls.

The treatment with toothpaste containing the composition also results in a reduction of dental caries.

Example 27

Acute Respiratory Disease

Patients with acute respiratory disease, including upper airway diseases, such as colds, are treated with the composition. Administration per os, intranasally or and installation into sinuses of 100 mg doses for 3-7 days results in a milder course of the viral infection. Secondary infectious complications are diminished, and the duration of the treatment is also diminished. Normalization of nasal breathing, the disappearance of nasal mucous swelling, the arresting of exudates from affect sinuses, and improved general condition and immune status is a common observation. Accelerated reduction in symptom complexes including joint pain, muscle aches, fevers, chills, and upper respiratory symptoms is also common.

Example 28

Ocular Diseases

Patients with various eye problems are treated by conventional methods, with one group receiving the composition in addition to the conventional treatment. Administration of the composition intraocularly at 18 mg for 5 consecutive days, or as installation into conjunctival cavity as drops for 5 days results in more rapid arresting of the inflammatory process and the increase in visual acuity, and the decrease of duration of treatment.

Example 29

Treatment of Wounds

The composition is used in patients with wounds of various origin, type and localization. The compound consisting of wound biopsy is administered topically as a single dose daily at 100 mg for 10 days. The use of the formulation speeds up (when compared to the control group) significantly wound healing, reduces therapy duration and prevents the development of infectious complications. Statistically fewer infections and reduced scarring is observed.

Example 30

Flu Vaccine Co-Administration

The product is given to persons in combination with the anti-flu vaccination delivered by air pressure. The compound dose is 50 mg delivered in a single oral dose for 3 consecutive days. After product use, a significant decrease of sickness rate for a period of 12 months is observed compared to controls who receive flu-vaccination alone without the composition.

Example 31

*Shigella*

A total of 10 patients infected with *Shigella* dysentery are examined. The composition prepared from stool sample of one the patients is administered orally in doses of 100 mg for 10 consecutive days with resultant normalization of fever, the reduction of toxemia, and the normalization gastrointestinal disorders and symptoms.

Example 32

Oral Rabies Vaccine for Dogs

The freeze-dried composition consisting of commercial vaccine suspension of SAG-2 strain of rabies virus of appropriate titer along with host cells in which virus is propagated is added at about 10 g per 100 g of dry mixture which has the following ingredients: lactose (28%); mannitol (70%); gum arabic (2%). The preparation is then dipped in a homogeneous mixture maintained at 56-60° C. of the following composition: paraffin 50° C. (52%), ethylenevinyl acetate copolymer (28%), vinyl acetate (6%), meat meal (23%), beef fat (17%), ROBERTET bacon flavor (2%). A dosage form is thus formulated into a product that has an appearance of an ordinary dog food pellet and is suitable for oral vaccination against rabies according to the invention.

Example 33

Dental Composition

A premix containing the active ingredients and excipients and having the following excipient composition: chlorhexidine diacetate (0.25%), methionine (3%), lactose (80%), beta-cyclodextrin (13%), dextran 70 (2%), pulverized silica (0.25%), aspartame (0.8%), sorbitan monopalmitate (0.7%) is prepared in an OLSA-type planetary mixer. The pulverulent mass is dry mixed for 30 minutes and then supplemented with water in an amount of 38 g per 100 g of dry mass, and blended for 1 hour at room temperature. The homogeneous suspension thus obtained is distributed into 1.5 $cm^3$ polyvinyl chloride cells. The cellular sheet containing the suspension is introduced into a freeze-dryer immediately after division, to be frozen at a temperature of −45° C. under atmospheric pressure, for about 3 hours. Following this step the composition is heat-dried for 12 hours under reduced pressure at a negative temperature, the temperature is reduced to 30° C., in steps of 5° C. The freeze-dried unit, extracted from the cell, is treated in a fluidized bed (GLATT GPC-15) with injection of air (100 liters/min) with a solution of hydrogenated castor oil (1 part), ethyl cellulose (2.5 parts), beeswax (3 parts), cetyl alcohol (1 part), groundnut flavor (0.15 part) in methylene chloride (80 parts).

Example 34

Cytomegalovirus Retinitis Treatment

Six patients with deteriorating eyesight due to CMV or cytomegalovirus infection took the vaccine of the invention for 2 weeks. Every patient reported improved and reversed symptoms of the disease. One patient who was blind and not able to see is now capable to count fingers and to see shades of light.

Example 35

Weight Gain

The composition of the invention is given to over 40,000 patients with HIV. The majority of them experience weight gain. The average weight is about 3 kg over 6 months. The increase in body weight is statistically significant (p=0.008). More emaciated patients however gain considerably more weight than patients who are so wasted. This example indicates that vaccine of the restores normal function of the gut and mucosal immune function.

Example 36

Quality of Life Improvement

About 400 patients' letters who request more supply of the vaccine are analyzed. Over 85% of patients notice significant improvement in their life quality. About 9% experience transient adverse effects and 6% have no noticeable changes. The most common reported symptoms include enhanced energy, ability to eat or improved appetite, ability to walk among those who are bed-ridden initially, ability to return to work, lack of headache, skin sores, oral thrush, etc.

The entire content of patents, references, and internet sites cited throughout this application are expressly incorporated herein by way of reference.

It should be understood that the examples and embodiments described herein are for illustrative purposes only and that various modifications or changes in light thereof will be suggested to persons skilled in the art and are to be included within the scope and spirit of the invention.

What is claimed is:

1. A composition comprising denatured hepatitis type B or type C viral pathogen, wherein the pathogens are denatured through a method comprising drying the pathogen and denaturing the resulting dried pathogen using heat alone, wherein the composition is formulated as an oral pill.

2. The composition process of claim 1, wherein the hepatitis viral pathogen is hepatitis B virus.

3. The composition of claim 1, wherein the hepatitis viral pathogen is hepatitis C virus.

4. The composition of claim 1, wherein said composition is formulated without an immune adjuvant.

5. The composition of claim 1, said composition further comprising hepatitis viral pathogen-infected denatured tissue.

6. A hepatitis immunogen comprising heat denatured hepatitis virus type B and type C, wherein the hepatitis B virus and hepatitis C virus are denatured through a method comprising drying the hepatitis B virus and hepatitis C virus and denaturing the resulting dried viruses using heat alone to produce the immunogen, wherein the immunogen is formulated as an oral pill.

7. The immunogen of claim 6, wherein said immunogen is formulated without an immune adjuvant.

8. The immunogen of claim 6, wherein the immunogen comprised in said pill is between about 0.0000001% to about 20% by weight.

9. An oral composition suitable for inducing an immune response in a subject, the composition comprising a first component comprising denatured hepatitis type B or type C viral pathogen, wherein the pathogens are denatured through a method comprising drying the pathogen and denaturing the resulting dried pathogen using heat alone, and a second component comprising a denatured pooled blood tissue from a host infected by hepatitis virus type B and type C.

10. The oral composition of claim 9, said composition further comprising calcium or magnesium, or both.

* * * * *

```
                              SEQUENCE LISTING

<160> NUMBER OF SEQ ID NOS: 1

<210> SEQ ID NO 1
<211> LENGTH: 39
<212> TYPE: PRT
<213> ORGANISM: Human immunodeficiency virus type 1

<400> SEQUENCE: 1

Lys Gln Ile Ile Asn Met Trp Gln Glu Val Gly Lys Ala Met Tyr Ala
1               5                   10                  15

Pro Pro Ile Ser Gly Gln Ile Arg Arg Ile His Ile Gly Pro Gly Arg
            20                  25                  30

Ala Phe Tyr Thr Thr Lys Asn
        35
```